United States Patent [19]
Carrino et al.

[11] Patent Number: 5,814,492
[45] Date of Patent: Sep. 29, 1998

[54] PROBE MASKING METHOD OF REDUCING BACKGROUND IN AN AMPLIFICATION REACTION

[75] Inventors: John J. Carrino; Thomas D. Brainard, both of Gurnee, Ill.

[73] Assignee: Abbott Laboratories, Abbott Park, Ill.

[21] Appl. No.: 912,976

[22] Filed: Aug. 13, 1997

Related U.S. Application Data

[63] Continuation of Ser. No. 478,152, Jun. 7, 1995, abandoned.

[51] Int. Cl.$^6$ .............................. C12P 19/34; C12Q 1/68; C07H 21/04; C07H 21/02
[52] U.S. Cl. ........................... 435/91.2; 435/91.1; 435/6; 435/5; 536/23.1; 536/24.3; 536/24.33; 536/24.32
[58] Field of Search .................................. 435/91.2, 91.1, 435/6, 5; 536/23.1, 24.3, 24.33, 24.32

[56] References Cited

U.S. PATENT DOCUMENTS

| | | |
|---|---|---|
| 4,683,195 | 7/1987 | Mullis et al. . |
| 4,683,202 | 7/1987 | Mullis . |
| 5,035,996 | 7/1991 | Hartley ......................................... 435/6 |
| 5,118,801 | 6/1992 | Lizardi et al. ............................. 536/27 |
| 5,142,047 | 8/1992 | Summerton et al. . |
| 5,166,315 | 11/1992 | Summerton et al. . |
| 5,185,444 | 2/1993 | Summerton et al. . |
| 5,215,899 | 6/1993 | Dattagupta .................................. 435/6 |
| 5,217,866 | 6/1993 | Summerton et al. . |
| 5,235,033 | 8/1993 | Summerton et al. . |
| 5,338,671 | 8/1994 | Scalice et al. . |
| 5,340,728 | 8/1994 | Grosz et al. ............................ 435/91.2 |
| 5,348,853 | 9/1994 | Wang et al. ................................ 435/6 |
| 5,418,149 | 5/1995 | Gelfand et al. ......................... 435/91.2 |
| 5,427,929 | 6/1995 | Richards et al. ........................ 435/91.2 |
| 5,427,930 | 6/1995 | Birkenmeyer et al. ................. 435/91.2 |

FOREIGN PATENT DOCUMENTS

| | | |
|---|---|---|
| 0320308 | 6/1989 | European Pat. Off. . |
| 0324616 | 7/1989 | European Pat. Off. . |
| 0439182 | 7/1991 | European Pat. Off. .......... C12Q 1/68 |
| 0497272 | 8/1992 | European Pat. Off. . |
| 0500224 | 8/1992 | European Pat. Off. . |
| 9001069 | 2/1990 | WIPO . |
| 9300447 | 1/1993 | WIPO . |
| 9325706 | 12/1993 | WIPO . |
| 0403630 | 2/1994 | WIPO . |
| 9402648 | 2/1994 | WIPO . |
| WO94/24311 | 10/1994 | WIPO .............................. C12Q 1/68 |
| 9429485 | 12/1994 | WIPO . |
| 9502690 | 1/1995 | WIPO . |
| 9506756 | 3/1995 | WIPO . |

OTHER PUBLICATIONS

Clark, J.M., "Novel non-templated nucleotide addition reactions catalyzed by procaryotic and eucaryotic DNA polymerases", Nucleic Acids Research, 16(20):9677–9686 (1988).
Abravaya et al. (1995) Nucl. Acids Res. 23:675–82.
Don et al. (1991) Nucl. Acids Res. 19:4008.
Chou, Q., et al. "Prevention of pre–PCR mis–priming and primer dimerization improves low–copy–number amplifications", Nucleic Acids Research, 20(7):117–1723 (1992).
Fahy, E., "Self–sustained Sequence Replication (3SR): An Isothermal Transcription–based Amplification System Alternative to PCR", PCR Methods and Applications, 1:25–33 (1991).
Kievits, T., "NASBA™ isothermal enzymatic in vitro nucleic acid amplification optimized for the diagnosis of HIV–1 infection", Journ. of Virol. Methods, 35:273–286 (1991).
Lizardi, P. M., "Exponential Amplification of Recombinant–RNA Hybridization Probes", Bio/Technology, 6:1197–1202 (1988).
Walker, G. T., "Isothermal in vitro amplification of DNA by a restriction enzyme/DNA polymerase system", Proc. Natl. Acad. Sci. USA, 89:392–396 (1992).

Primary Examiner—W. Gary Jones
Assistant Examiner—Dianne Rees
Attorney, Agent, or Firm—Thomas D. Brainard; Paul D. Yasger

[57] ABSTRACT

A method for reducing background caused by target-independent generation of amplification products, typically the products of a ligase chain reaction or a polymerase chain reaction, involves chemically "masking" or blocking the amplification probes or primers so that they cannot be extended or ligated until the occurrence of a triggering event which can be delayed until the amplification reaction is begun. The probe masks take the form of complementary blocking oligonucleotides that are incapable of serving as template themselves and inhibit random tailing of the probe/primers. The blocking oligo masks are denatured from the probes during amplification and preferably are effectively eliminated from competing for probes in the amplification reaction.

20 Claims, 11 Drawing Sheets

☐ = stopbase(s), blocking group, PNA, etc.

IMx^R Rate      FIG. 9A

IMx^R Rate

PROBE MASKING METHOD OF REDUCING BACKGROUND IN AN AMPLIFICATION REACTION

This application is a continuation of U.S. patent application Ser. No. 08/478,152, filed Jun. 7, 1995, which is now abandoned.

This invention relates to a method for reducing the undesired background signal caused by target-independent generation of amplification products, typically the products of a ligase chain reaction or a polymerase chain reaction. More specifically, the invention relates to a method of "masking" or blocking the amplification probes or primers so that they cannot be extended or ligated until the occurrence of a triggering event, which can be delayed until the amplification reaction is begun. The probe masks take the form of blocking, complementary oligonucleotides that are removed upon initiation of amplification.

BACKGROUND OF THE INVENTION

Amplification techniques for the detection of target nucleic acids in biological samples offer high sensitivity and specificity for the detection of infectious organisms and genetic defects. Copies of specific sequences of nucleic acids are synthesized at an exponential rate through an amplification process. Examples of these techniques are the polymerase chain reaction (PCR), disclosed in U.S. Pat. Nos. 4683,202 and 4,683,195 (Mullis); the ligase chain reaction (LCR) disclosed in EP-A-320 308 (Backman et al); and gap filling LCR (GLCR) or variations thereof, which are disclosed in WO 90/01069 (Segev), EP-A-439-182 (Backman, et al) and WO93/00447 (Birkenmeyer et al.). Other amplification techniques include Q-Beta Replicase, as described in Lizardi, et al., *Bio/Technology*, 6:1197 (1988); Strand Displacement Amplification (SDA) as described in EP-A-497 272 (Walker), EP-A-500 224 (Walker, et al) and in Walker, et al., in *Proc. Nat. Acad. Sci. U.S.A.*, 89:392 (1992); Self-Sustained Sequence Replication (3SR) as described by Fahy, et al. in PCR Methods and Applications 1:25 (1991); and Nucleic Acid Sequence-Based Amplification (NASBA) as described in Kievits, et al., *J. Virol. Methods*, 35:273–286 (1991).

One of the greatest advantages of these amplification methods is the generation of million-fold copies of the desired nucleic acid sequence by an exponentially repetitive process. Such exponential reactions compound greatly the potential for development of undesired background created by the template independent generation of amplification product. High background signal limits the detection sensitivity of any amplified assay. It is presently believed that template-independent product can result from the incubation of reagents at room temperature.

Several methods have been developed to address the non-specific signal generated by target independent creation of amplification product. For example, in polymerase chain reactions (PCR) an internal hybridization probe is frequently used to confirm the identity of the amplification product. In addition, a technique known as "hot start" PCR has also been used to reduce background and improve specificity. In hot start PCR, the reaction is prevented until the temperature is raised at least to the annealing temperature. This may be accomplished by delaying addition of one of the reagents (e.g. the polymerase) or by initially segregating the reagents. One method for segregation employs a paraffin or other meltable septum dividing the enzyme from the other reagents as taught in Chou et al, *Nucl. Acids Res.* 20:1717–1723 (1992). Upon heating to dissociate target the septum is melted and the reagents combine, but not until a relatively high temperature has been reached. In another variation described in U.S. Pat. No. 5,338,671 (Christy, et al), a heat labile antibody binds to a thermostable polymerase enzyme, thereby blocking its activity at low temperatures. As the reaction is heated, the antibody is permanently inactivated and the polymerase becomes active.

In a recent development described in U.S. Pat. No. 5,438,853 (Wang, et al. issued Sep. 20, 1994), energy sink oligonucleotides are employed to prevent PCR primers from hybridizing and extending inadvertently on non-target templates. The energy sink oligos have modified 3' ends to prevent extension thereof and are preferably 5' end recessed with respect to the primer to which they hybridize.

In ligase chain reactions (LCR), template-independent formation of amplification product was largely attributed to blunt-end joining of the pairs of complementary probes. (Backman, et al. EP-A-0 439 182). Gap LCR and other variations on LCR were developed to avoid such blunt ends. But applicant has found that even with gapped LCR probes having 5' recessed ends (vis-a-vis the complementary LCR amplification probe), some template-independent generation of amplification product is seen under extreme conditions. This is believed to be due to the ability of the polymerase, albeit inefficiently, to tail randomly an upstream LCR probe when complexed with its complementary probe, thereby potentially creating sticky ended LCR probes which might contribute to background.

Thus, an important objective of the invention is to reduce further the small amounts of template-independent background still being generated in gap LCR. A corollary objective is to improve the sensitivity of assays by reducing undesired background.

These and other objectives are met in the present invention as described below.

SUMMARY OF THE INVENTION

In a first aspect, the invention provides a method for amplifying nucleic acids involving repeatedly extending one or more amplification probes by the template directed addition of individual nucleotides or oligonucleotide segments, the improvement comprising:

a) prior to initiating an amplification reaction, providing at least one amplification probe in a masked form, the mask consisting essentially of a blocking oligo hybridized with said amplification probe to form a masked probe heteroduplex, wherein said blocking oligo:amplification probe heteroduplex has a $K_{50bp}$ such that $K_{50bp}$ is less than $K_{50pt}$ where $K_{50pt}$ is the $K_{50}$ of the target strand:amplification probe homoduplex, and wherein said blocking oligo inhibits extension of the amplification probe;

b) denaturing the blocking oligo from the amplification probe to unmask the amplification probe; and c) carrying out the amplification reaction with the unmasked amplification probe.

In a preferred further aspect, the invention provides an additional step of inhibiting the blocking oligo from interfering in the amplification reaction without physically removing the blocking oligo from the reaction mixture. This may be done by using a blocking oligo that has at least one deletion or mismatch with respect to the amplification probe so as to effect a 3° to 15° C. lowering of the Tm; or by hybridizing the blocking oligo to a complementary blocking oligo to form stable blocking oligo homoduplexes which effectively sequester both blocking oligos from the reaction. Blocking oligo:blocking oligo duplexes may be stabilized by employing tails (e.g. 5–30, preferably 5–20 nucleotides long) on the blocking oligos which are complementary to each other, but not to target, to increase the Tm of the blocking oligo homoduplexes; or by covalently attaching the blocking oligos together.

In another aspect, the invention provides a composition of matter useful for practicing the methods, comprising:

at least two amplification probes; and at least one, optionally two, blocking oligos hybridized with said amplification probes to form at least one masked probe duplex, wherein under storage conditions said amplification probes are prevented from random extension and wherein, in the presence of a polymerase and nucleotides under amplification reaction conditions, said blocking oligo inhibits extension of the amplification probe. The preferred compositions have features identified above for performing preferred methods. In addition, kits for performing the methods may consist of the compositions and necessary reagents, such as a polymerase and/or a ligase.

BRIEF DESCRIPTION OF THE FIGURES

In all FIGS, A' and B are complementary sequences of A and B', repectfully.

FIGS. 9A and B are graphical representations of the data presented in Table 1-A of example 1. FIG. 9A is a representation of the rate range when no target and no blocking oligo is present.

DETAILED DESCRIPTION OF THE INVENTION

A. TERMINOLOGY

Figure 1:
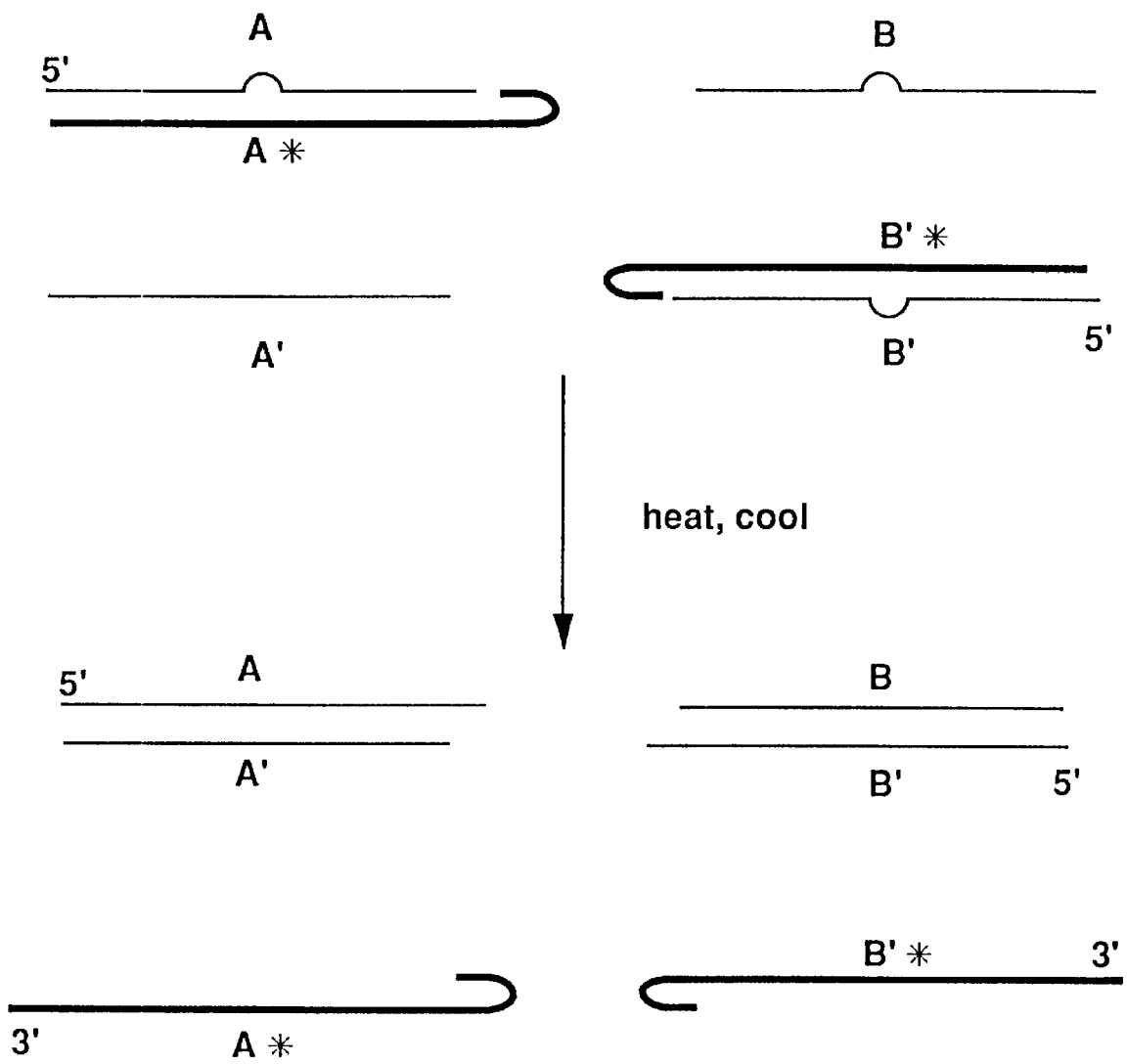
FIG. 1 is a schematic representation of one embodiment of the invention using two 5' hairpin blocking oligos (A* and B'*) on the extendible upstream probes (A and B') in gap LCR. Interference control is provided by a deletion, depicted by the bubble in the probe, which makes the probe:oligo heteroduplex less stable than the probe:probe or probe:target homoduplexes, as these terms are defined herein.

"Background signal" or just "background" refers to signal that is generated in the absence of target. Regardless of the detection system employed, one major cause of background in amplification reactions is the formation of detectable amplification product in a target-independent manner. In this application, "target-independent" is synonymous with "template-independent" since the amplification reactions involve template-directed extensions and/or ligations using target, or its equivalent, as template. Background may be generated in PCR when primers find non-target template positions having sufficient complementarity to permit hybridization and extension under the reaction conditions. In LCR, background may be generated when the probes use themselves as template or ligate in the absence of a template.

The terms "probe," "amplification probe," "target probe" and "primer" are variously used herein to denote the polynucleotide sequences that are designed to amplify specifically and detect a target of interest; while the term "oligo" (or "blocking oligo") is reserved for description of the polynucleotides that block the probes and primers from creating extension products. Duplexes consisting of a blocking oligo hybridized to either target or a target probe and are referred to herein as "heteroduplexes"; while target:probe duplexes, target:target duplexes, probe:probe duplexes and blocking oligo:blocking oligo duplexes are all referred to herein as "homoduplexes". It will be understood that this use of the terms "heteroduplex" and "homoduplex" differs somewhat from the more conventional usage which refers to DNA:DNA double strands as homoduplexes and to RNA:DNA double strands as heteroduplexes. The terms "heteroduplex" and "homoduplex" have the meaning given above regardless of the substituent at the 2' position of the nucleotides, and are introduced herein for convenience. As will be realized, after the initial blocking oligos are removed and amplification has commenced, formation of homoduplexes are always preferred over the formation of heteroduplexes.

Polynucleotides and "oligos" used in the invention include any polymeric structure which links purine and/or pyrimidine base moieties together in a predetermined sequence. The exact nature of the polymeric structure is not critical, provided it links the base moieties with spacing and steric freedom appropriate to permit the base moieties to engage in conventional base pairing (e.g. A/T and G/C) with natural DNA or RNA. Exemplary polymeric backbone structures include, for example, sugar-phosphate linkages (as are found in naturally occurring DNA or RNA); uncharged alkyl analogs such as methyl phosphonates, and phosphotriesters; peptide bond analogs thereof (as is disclosed in WO 93/25706); and morpholino analogs thereof (as disclosed in U.S. Pat. Nos. 5,142,047, 5,235,033, 5,166,315, 5,217,866 and 5,185,444).

By "amplification reaction" is meant a reaction that produces multiple copies of a sequence of nucleic acid by repeated extension of a probe or primer. "Extension" may occur by virtue of polymerization of individual nucleotide monomers, as in PCR, or it may occur by the addition of prefabricated oligonucleotide segments, as in LCR, or by a combination of these, as in gap LCR or Repair Chain Reaction (RCR). Though not essential to the invention, ideally the extension reactions are performed repeatedly, and the extension products themselves serve as templates to produce an exponential generation of amplification products with respect to the cycle repeats.

As noted above, background is generated when the extension begins and amplification product is formed independent of target. Since existing techniques have already reduced background somewhat, it is sometimes necessary to "push" an amplification reaction to extreme conditions to generate background at observable levels. This simply means that more cycles may be performed than would normally be necessary to detect target. "Pushing" to extreme conditions may involve particularly high enzyme and/or probe concentrations or low temperature preincubations of all reagents necessary for amplification.

The stability of polynucleotide duplexes is known to be affected by several factors, including length, G:C content, charge of the polynucleotides, ionic conditions and temperature. In each case, as the particular factor varies in an increasing direction, the degree of hybridization either increases or decreases (depending on the factor) to produce a generally sigmoidal curve. The sum of all these factors (depicted herein as "K") is a measure of the stability of the duplex. The point at which the polynucleotides are 50% hybridized and 50% unhybridized is referred to herein as the $K_{50}$. This is a general case of and directly analogous to the well known Tm (where only the temperature factor is varied). For a given probe set (which determines length and G/C content) and ionic conditions, $K_{50}$ corresponds to Tm and thus Tm is generally substituted for $K_{50}$. All Tm's given herein are determined spectrophotometrically.

The following table will assist in differentiating all the possible homo- and heteroduplexes and the $K_{50}$ or Tm of each possible pair.

| Duplex formed | Shorthand | Duplex type | $K_{50}$ | Tm |
|---|---|---|---|---|
| Target-Target (original ds) | tt | homoduplex | $K_{50tt}$ | $Tm_{tt}$ |
| Probe-Probe (in LCR only) | pp | homoduplex | $K_{50pp}$ | $Tm_{pp}$ |
| Probe-Target (all) | pt | homoduplex | $K_{50pt}$ | $Tm_{pt}$ |
| Blocking Oligo-Blocking Oligo* | bb | homoduplex | $K_{50bb}$ | $Tm_{bb}$ |
| Probe-Blocking Oligo (all) | bp | heteroduplex | $K_{50pb}$ | $Tm_{pb}$ |
| Blocking Oligo-Target | bt | heteroduplex | $K_{50bt}$ | $Tm_{bt}$ |

*Only where (i) complementary amplification probes are used, both of which are blocked, or (ii) complementary blocking oligos span the gap of an LCR probe set.

These duplex variations and the relative stability of each are discussed in detail below in connection with interference controls.

B. BLOCKING TECHNIQUES

At the heart of the invention are the blocking oligos. As mentioned, these are polynucleotides that are complementary to the amplification probes, but which inhibit extension of the amplification probe. Such inhibition should be without regard to whether the extension would be template-directed or random tailing. Polymerases known to date extend or tail from the 3' end of a probe. For this reason, the invention is described in terms of blocking oligos that have masking means at their 5' ends to prevent such extension or tailing of PCR primers and the "upstream" probes of an LCR set. Of course, if polymerizing enzymes are discovered which extend from the 5' end, the concepts of the invention may be reversed to work in the opposite direction as well.

It has been shown by Clark, *Nucl. Acids Res.* 16 (20):9677–9686 (1988) that when complementary, blunt-ended probe duplexes are incubated with 2'-deoxyribonucleotide triphosphates ("dNTPs") and polymerase, the polymerase will extend the 3'-hydroxyl probe ends even in the absence of any template. This work is confirmed in our hands by example 8. The efficiency of "tailing" varies slightly with the dNTP added (dATP being added most easily), but even at low efficiencies some background can result, particularly where randomly tailed ends introduce a sticky-end overlap between two "upstream" LCR probes. Applicant has found that this tailing reaction occurs to some degree even with non-blunt probe pairs having 3' overhangs, e.g. of 1 to about 3 bases. Elimination or reduction of this low efficiency random extension is a purpose of the blocking oligos.

Blocking oligos are thus designed and synthesized to block the extension of the amplification probes; in other words, to "mask" the amplification probe. The blocking oligos are generally complementary to the respective probes to be masked, although perfect complementarity is not required. As discussed below in connection with interference control, perfect complementarity is to be avoided in some instances. The blocking oligo need only be sufficiently complementary that, under storage conditions, the amplification probe: blocking oligo heteroduplexes essentially do not dissociate. Storage conditions typically include temperatures no higher than ambient, and usually include refrigeration of reagents. Such complementarity is sufficient to mask the reagent probes, i.e. to prevent the probes from finding true target or closely related sequences, or, in the case of LCR, from finding target or complementary amplification probes, prior to initiation of the amplification reaction.

In addition to being complementary, blocking oligos carry a masking means for inhibiting the extension of the corresponding amplification probe. Masking means can be achieved through a variety of mechanisms, depending on the circumstances. Several exemplary blocking mechanisms are discussed below.

In some embodiments, a 5' overhang exists with respect to the 3' extendable end, but the overhang is incapable of serving as template to direct extension for one or more reasons. For example, the overhang may comprise a stopbase which prevents template-directed extension due to enzyme fidelity; it may exhibit a secondary structure that sterically inhibits the polymerase from recognizing or acting on the substrate to accomplish template-directed extension; or it may comprise a string of modified bases that fail to serve as template for directing extension. Each of the above variations, which may be used in combination with one another, are explained below.

Figure 2:
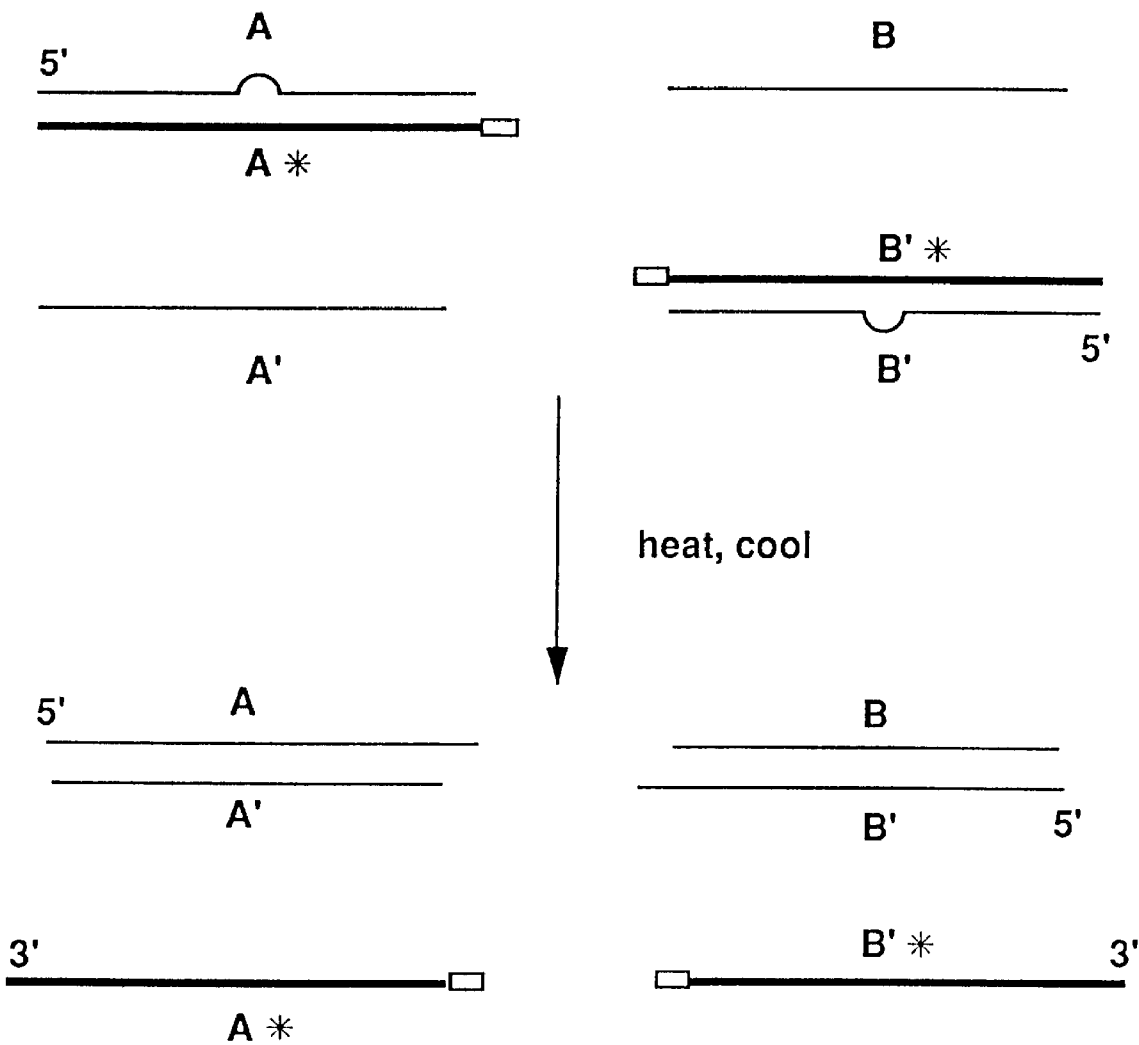
FIG. 2 is a schematic representation of another embodiment of the invention using two 5' stopbase blocking oligos (A* and B'*) on the extendible upstream probes (A and B') in gap LCR. Interference control is provided by a "bubble" deletion as in the embodiment of FIG. 1.
Figure 3:
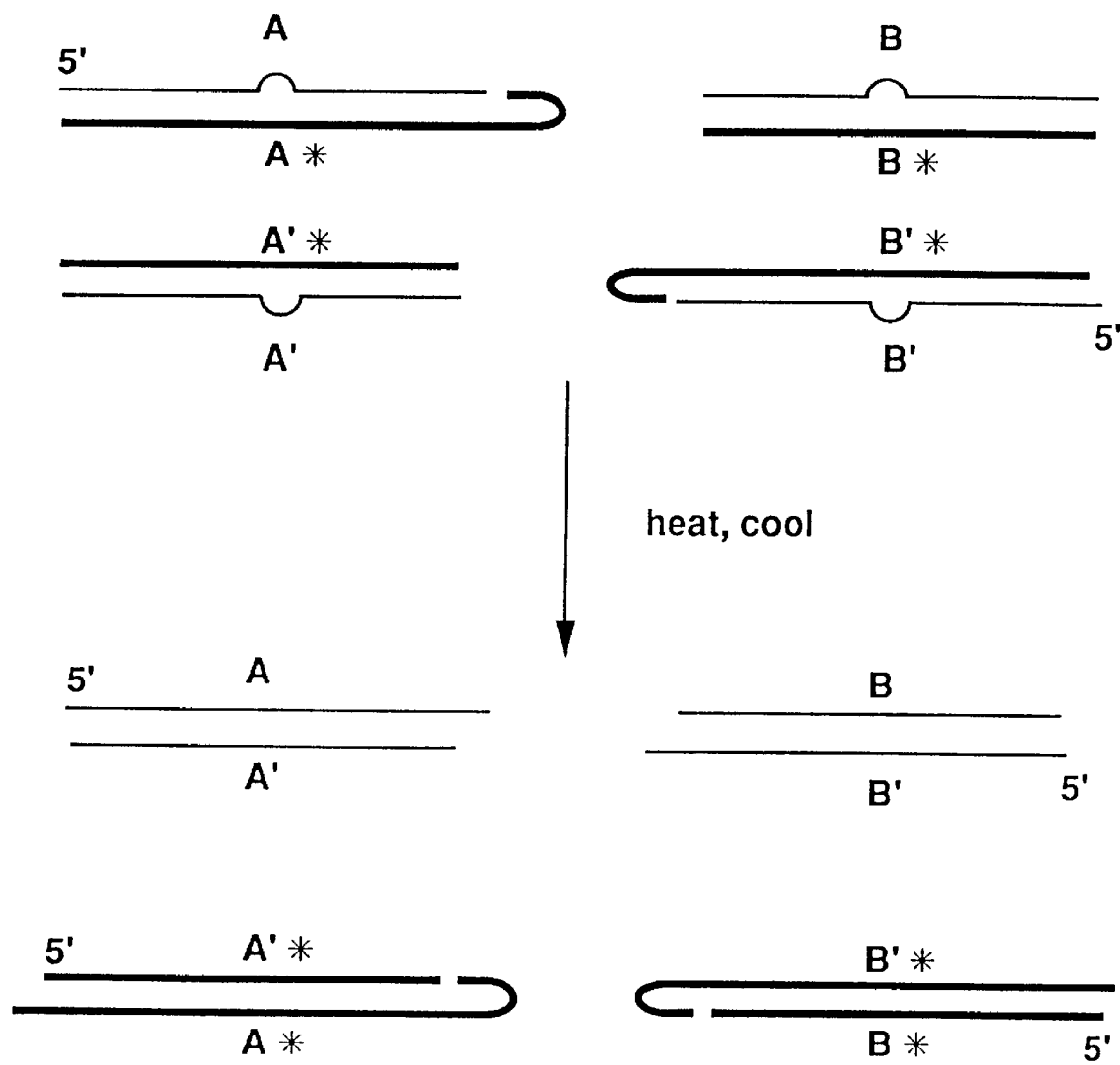
FIG. 3 is a schematic representation of another embodiment of the invention using four blocking oligos (indicated by asterisk "*"), one on each of the four probes used in gap LCR. Interference control is provided by a "bubble" deletion as in FIG. 1 so that the probe:oligo heteroduplex is less stable than the probe:probe or probe:target homoduplexes. In addition, when the bubble deletions are aligned the complementary blocking oligos can form oligo:oligo homoduplexes than are more stable than the oligo:probe heteroduplexes.
Figure 4:
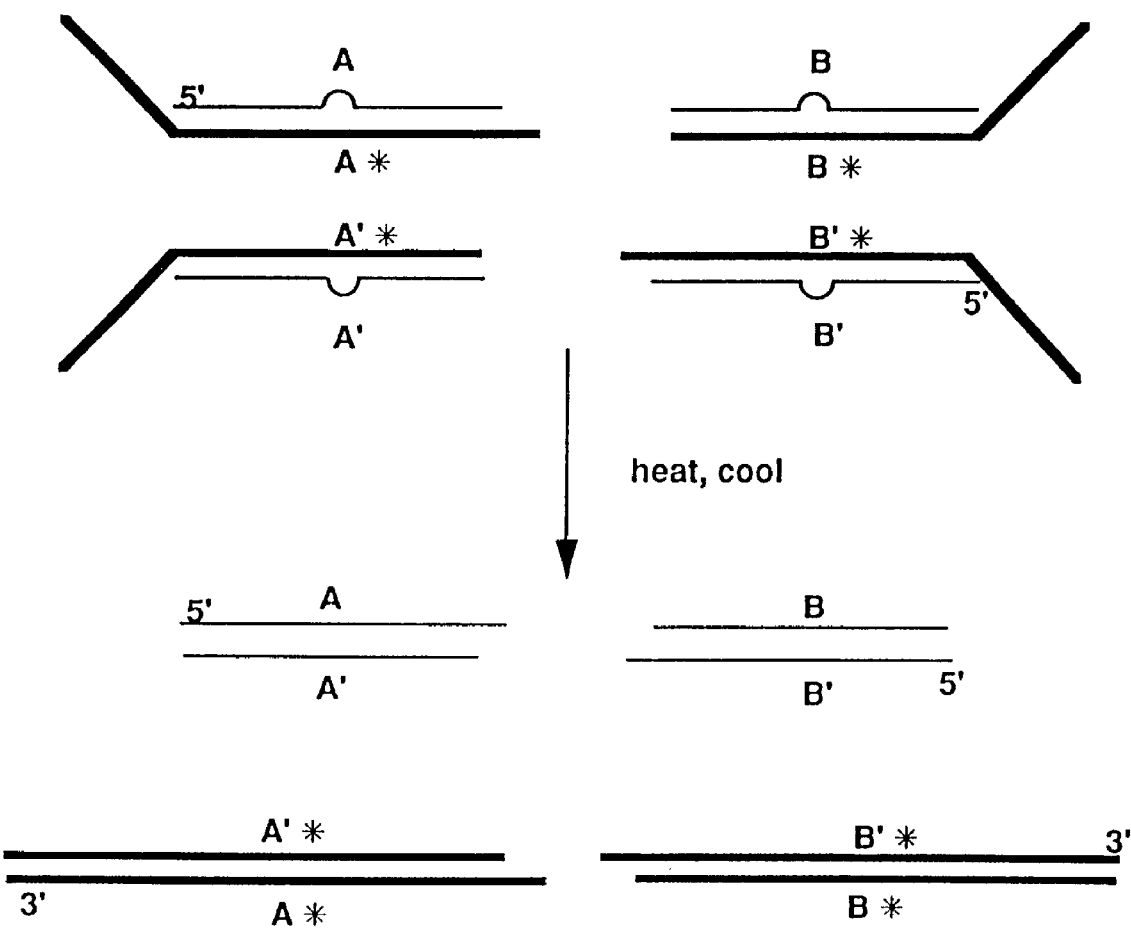
FIG. 4 is a schematic representation of another embodiment of the invention using four blocking oligos (indicated by asterisk "*"), one on each of the four probes used in gap LCR. In this case, interference control is provided by a "bubble" deletion (as in FIG. 1) and by the "tail" portions of the blocking oligos. These tails ensure that the oligo:oligo homoduplexes are stable relative to the probe:oligo heteroduplex. It is also true that the probe:oligo heteroduplex is less stable than either the probe:probe or probe:target homoduplexes.

In a first variation (see FIGS. 2, 5 and 7), normal nucleotides of the 5' end of the blocking oligo extend beyond the 3' end of the amplification probe, but a stopbase (defined below) is used to prevent extension. Extension cannot proceed due to the fidelity of the polymerase in following the template and the absence of the needed dNTP. The 5' extension in this variation need be only one additional base-the stopbase. However, in synthesis of oligonucleotides, the presence in small quantities of the n−1 failure product is nearly unavoidable and difficult to purify away from the desired product. For this reason longer extensions, for example 3–15 bases, were designed with the first one or more positions past the 3' end of the amplification probe being a stopbase. In a further optional variation, the 3–15 base extension is designed to fold back on itself as a hairpin, thus employing a secondary structure mask in combination with a stopbase mask. The hairpin end may optionally be crosslinked to itself to prevent unfolding.

A stop base refers to a base or nucleotide in the template to which a potential primer molecule (e.g. amplification probe or primer) might hybridize, for which the complementary dNTP is omitted from the amplification reaction mixture. Thus, while we speak of a stop base as being present in a template or a blocking oligo, stop base derives its meaning in the context of an amplification extension reaction having in mind a particular template and the dNTP mixture that would be needed to extend on that template. For example, if a gap LCR reaction mixture contains dATP and dCTP to fill the gap between probes on the target-template, either A or C, or both, can serve as a stop base since they direct the addition of T and G, respectively, both of which are absent from the reaction mixture. If A and T are needed for extension, then C or G can serve as stop base. In the case of known polymerases, the stop base must occur in the template at the first position past the 3' end of the probe. A stop base may also occur elsewhere in the blocking oligo.

It will be noted that the stopbase mechanism for prevention of extension is useful when less than all four dNTPs are present in the reaction. Thus, the stop base technique is particularly useful in gap LCR, wherein the typically short gaps of 1–5 bases can easily be filled with 3 or fewer types of dNTPs.

Strategies for selecting targets having suitable gap configurations are taught in the prior art, e.g. WO 93/00447 (Abbott). The technique is useful in PCR where the template sequence is known and, regardless of its length, is composed entirely of just three (or fewer) of the four nucleotide types. This configuration, while potentially rare in nature, is nonetheless suitable for the invention since the base not used in completing the template can serve as the stop base by omitting its complementary base from the reaction mix.

Figure 5:
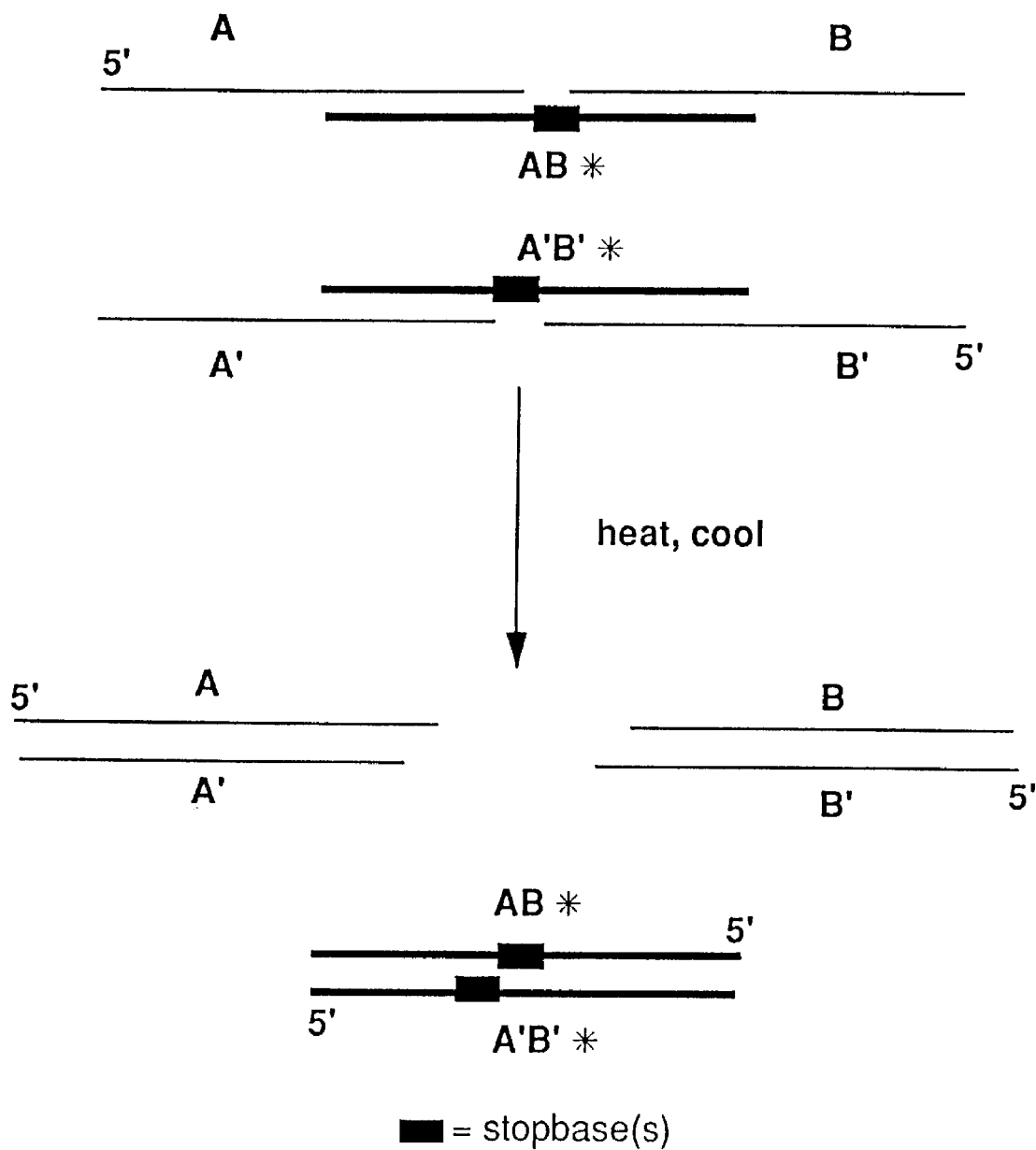
FIG. 5 is a schematic representation of another embodiment of the invention using two blocking oligos (AB* and A'B'*) which span the gap of a set of four LCR probes. A stopbase is included in the blocking oligo to prevent extension of the upstream probes. In this embodiment interference control is provided by carefully selecting probe and oligo lengths so that the probe:oligo heteroduplexes are less stable than the probe:probe or probe:target homoduplexes. For example, the blocking oligos can form an oligo:oligo homoduplex that is more stable than an oligo:probe heteroduplex because the oligo and probe hybridize to one another over only about half their lengths.

In a special case of the stopbase masking means in LCR, a single pair of blocking oligos can mask both the upstream and downstream probes simultaneously. This variation is depicted in FIG. 5. The blocking oligos span the ligation junction. In order for the blocking oligos not to serve as template themselves, they must be designed with stopbases to the 5' side of the base which hybridizes to the 3' terminus of the upstream amplification probe.

A second masking technique employs the secondary structure of an extension in the blocking oligo and is depicted in FIGS. 1, 3, 6 and 8. The extension should not be complementary to the target. Again, for the directionality of known polymerases, the extension is formed in the 5' end of the blocking oligo so that the secondary structure occupies the space at the 3' end of the amplification probe and interferes with any enzyme catalyzed extension, whether template-directed or random. An example of such a secondary structure is a hairpin turn. In this simplest of secondary structures, the extension is designed to be self complementary at its ends and long enough to provide a hinge region so that the self complementary ends can fold back over one another and anneal. The hairpin end may optionally be crosslinked to itself to prevent unfolding. In this configuration it is generally preferable that the 5' terminal base lie adjacent the 3' terminal base of the probe to provide the most efficient mask. However, in LCR mixtures containing ligase the 5' end of the blocking oligo should not be phosphorylated or it should terminate with at least one base between it and the amplification probe in order to avoid inadvertent ligation of the amplification probe to the folded portion of the blocking oligo. If a gap is present between the ends of the probe and the hairpin turn, a stop base should be included in the blocking oligo at the end of the extendible probe.

The length of the 5' extension which forms the secondary structure is not crucial, provided it is at least the minimum length to form a stable hairpin (a minimum of about 7 or 8 nucleotides). In cases where hybridization sequestration is used as interference control in LCR (see below), the hairpin may be relatively long and is preferably complementary to a similar hairpin on the blocking oligo of the complementary amplification probe, thereby using the length of the hairpins to contribute to the Tm stabilization of the blocking oligo homoduplex, without affecting the Tm of the blocking oligo:probe heteroduplex. Hairpins used in sequestration interference control are preferably not crosslinked.

For PCR and gap LCR using hairpin-like secondary structures, it may be preferable to employ a polymerase having little or no 5' to 3' exonuclease activity, although the data of example 9 suggest that displacement and extension through the hairpin can occur. Alternatively, the 5' end of the hairpin might carry a blocking moiety, as described below, to reduce the likelihood of degradation by exonuclease activity. As shown in example 9, the use of hairpin secondary structures alone provided limited blocking ability, but the combination of hairpins and 3' mismatches provided excellent blocking. Secondary structure may thus be used in combination with mismatch and/or stop base blocking techniques.

A variation of secondary structure masks involves blocking oligos that are formed into secondary structures and held there by crosslinking or other means. For example, to prevent displacement of a standard hairpin end, the hairpin can be locked closed by intercalating agents which crosslink the paired bases of the hairpin to covalently join them and hold the hairpin closed. Such intercalating and crosslinking agents are well known in the art and include psoralens and related compounds.

A third variation of probe masking involves the use of extensions that are not recognized as substrates by the extending enzymes, typically a polymerase. (see FIG. 2) Such extensions generally include one or more monomers of base moieties linked by means other than sugar-phosphodiester bonds. Examples include modified nucleotides or nucleic acid analogs such peptide bond linked monomers (the so-called "PNAs" of WO93/25706) and those linked by morpholino structures as taught in U.S. Pat. Nos. 5,142,047, 5,235,033, 5,166,315, 5,217,866 and 5,185, 444, each of which is incorporated herein by reference. In each case one or more such analogs are employed much like a stopbase to prevent extension. Although it is believed that a single such analog monomer will inhibit background extension, it may be necessary or desirable to use several. It is contemplated also that the entire blocking oligo may be formed from such analogs.

In a fourth variation (not truly a 5' overhang type however) probe masking is accomplished by designing the blocking oligo to have a mismatched base at or near the 3' end of the blocked amplification probe. Extension generally requires a primed template in which the 3' end of the primer is base paired with the template. Efficiency of priming falls considerably when the first or second base at the 3' end is not correctly base paired.

A final masking technique employs a blocking molecule or moiety attached at or near the end (5' end for known polymerases) of the blocking oligo. Such a blocking moiety masks the amplification probe by steric considerations; i.e. the size, bulk and positioning of such a molecule interferes with the polymerase's ability to use the duplex as a substrate to extend the end of the amplification probe. Thus this mechanism is similar to secondary structure masks. Exemplary blocking moieties include haptens and certain chemical coupling groups.

Numerous haptens are known in the art and illustrative haptens include many drugs (e.g. digoxin, theophylline, phencyclidine (PCP), salicylate, etc.), T3,biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Certain haptens described herein are disclosed in co-pending, co-owned patent applications U.S. Ser. No. 08/049,888 (adamantaneacetic acids), U.S. Ser. No. 08/084,495 (carbazoles and dibenzofurans), both deriving priority from Dec. 17, 1991. Methods of adding haptens to probes are well known in the literature.

Figure 6:
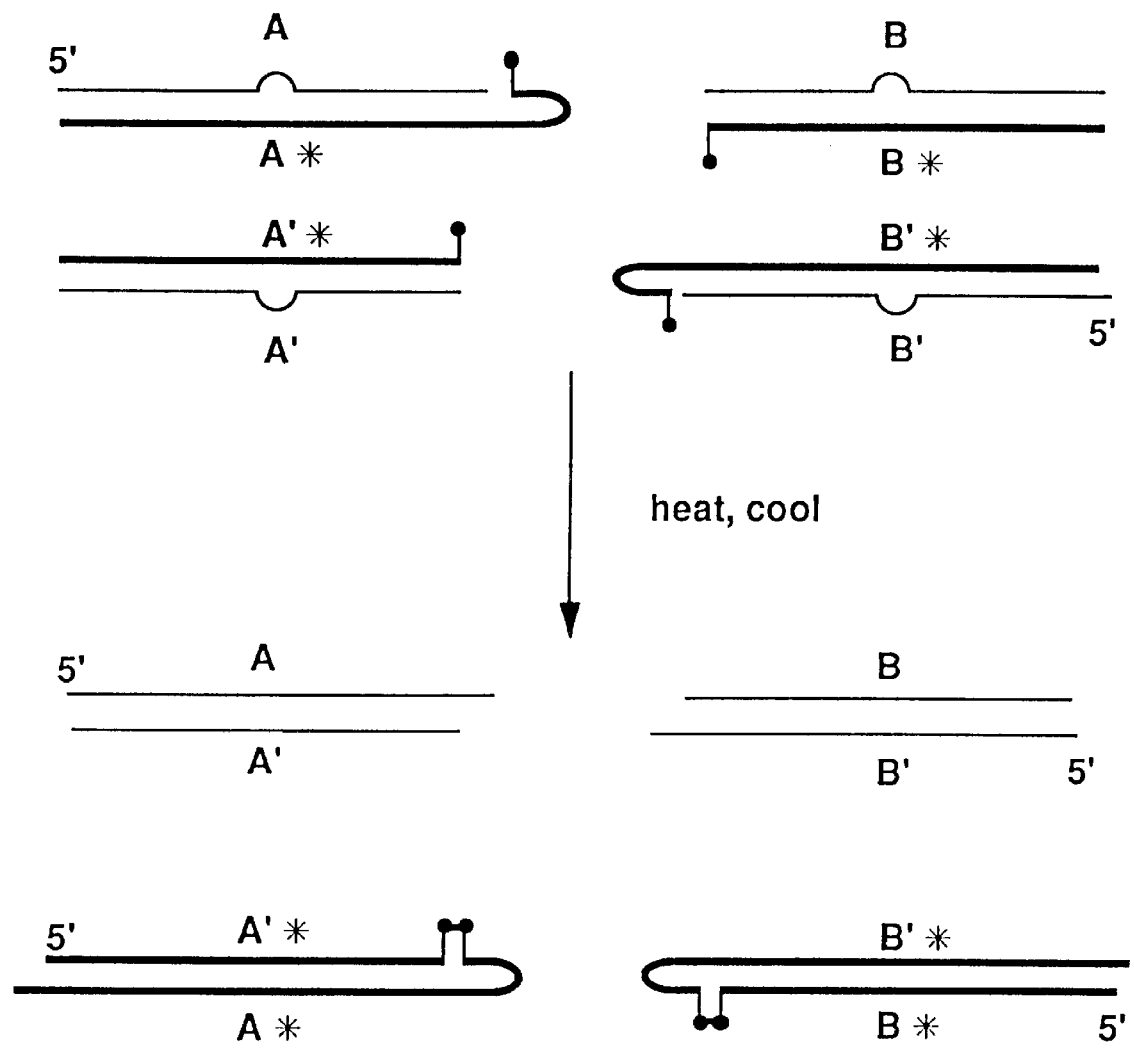
FIG. 6 is a schematic representation of another embodiment of the invention using four blocking oligos (indicated by asterisk "*"), one on each of the four probes used in gap LCR. In this case, interference control is provided by a "bubble" deletion and by chemical groups on each of the blocking oligos. These chemical groups are activated to covalently attach the blocking oligos to each other once they are separted from their respective amplification probes and allowed to hybridize to one another. In a variation of this, the hairpin blocking oligo may be crosslinked in the hinge region to prevent "unbending" of the hairpin.

Finally, chemical coupling groups such as are disclosed in EP-A-0 324 616 (Amoco), WO90/01069 (Segev), and WO 94/29485 (Segev) can also serve as a masking group (see FIG. 6). These compounds function as sterically blocking groups. Other reasons for using such chemical groups are discussed below in connection with interference control.

The above discussion has focused on blocking the 3' ends of probes that are normally extended. This is appropriate for both PCR and gap LCR. In LCR, however, it is also possible to block the 5' ends of the other two probes. The probes which are extended to fill the gap in gap LCR have been referred to in the art as the "upstream" probes; while the other probes (to which the extended upstream probes are ligated) have been referred to as "downstream" probes. Upstream probes may be blocked in the manner described above. For blocking the downstream probes, any of the above techniques may be employed, but a simple 3' phosphate is sufficient to block ligation extension of the amplification probe as well as polymerization extension of the blocking oligo itself. In general it is always preferable to block the 3' ends of the blocking oligos also, as they too might serve as primers for extension. In some cases, it may be preferred to use a chemical coupling moiety at the 3' end of the blocking oligo masking a downstream probe. This is described below.

In PCR, generally both primers should be blocked, unless it is known that the background is all attributable to just one of the primers. In LCR it is preferable to block all four probes. In gap LCR it remains preferable to block all four probes to obtain the benefit of masking both the polymerization extension and the ligation extension. Where only two probes are blocked, it is preferable to block the two "upstream" probes whose 3' ends are extended to fill the gap. As seen from the examples, masking of these two probes reduces background more efficiently than masking of the "downstream" probes only. Though perhaps not immediately appreciated, some blocking value is obtained by blocking only the downstream probes in a gap LCR amplification reaction (see Example 5). This is believed to be due to the need for a duplex for random tailing to occur. If the downstream probe is masked, the complementary upstream probe remains single stranded and is less likely to be tailed.

As mentioned, it is possible to use combinations of the above probe masking techniques in the same blocking oligo or on different blocking oligos of the same set. As shown in the examples, one might use a hairpin extension and a stop base within the same blocking oligo. Similarly, one might utilize a hapten or other blocking moiety on a different amplification probe in the same amplification probe set. Also useful, are hairpin masks in combination with mismatch masks. Of course, other permutations are easily within the grasp of one skilled in the art.

C. INTERFERENCE CONTROL TECHNIQUES

It should be understood that once the blocking oligos have served their purpose of masking the probes prior to amplification, it is desirable to effectively remove them from the reaction mix in order to prevent them from interfering with the amplification reaction. Such interference can arise when, for example, the blocking oligos compete with the true targets for the amplification probes, or when the blocking oligos compete with the amplification probes for true targets. Effective removal of the oligos from the amplification reaction can take place by any one or more of several techniques. The techniques fall generally into two categories: (1) those taking advantage of differential $K_{50}$ (or Tm), thus requiring that the blocking oligo heteroduplexes (both bt and bp) be less stable than the corresponding homoduplexes, especially the probe:target homoduplex; and (2) those that degrade the masking or blocking oligo upon initiation of amplification.

Duplex stability considerations are important to practising the first type of interference control. Most generally, heteroduplexes should be less stable than homoduplexes, regardless of type. More particularly, both the blocking oligo:target ("bt") and the blocking oligo:probe ("bp") heteroduplexes should have a $K_{50}$ or Tm less than the least of the $K_{50}$ or Tm's for the target:target ("tt"), the target:probe ("tp") and the probe:probe ("pp") homoduplexes. In formed, the Tm of these should be either greater than or less than (but not equal to) the Tm of either heteroduplex. These are described in more detail below, but can be summarized with the following representations, it being understood that $K_{50}$ is similarly summarized:

(1) It is most important that both $Tm_{bp}$ and $Tm_{bt}$ be less than $Tm_{pt}$;

(2) Generally, $Tm_{bp} \equiv Tm_{bt}$ and $Tm_{pt} \equiv Tm_{pp}$; and, (3) It is generally preferred that $Tm_{bb}$, if it exists, exceeds $Tm_{bp}$.

In a first technique, shown in FIGS. 1–5 and 6–8, the sequence of the amplification probe is made perfectly complementary to the target to maximize the Tm of the pt homoduplex ($Tm_{pt}$). The Tm of the bp heteroduplex (and consequently also the bt heteroduplex) is kept lower than $Tm_{pt}$ by designing the blocking oligo sequence to be complementary but for a deletion, addition or mismatch of one or more bases, generally near the middle of the oligo. This causes a "bubble" in the blocking oligo:probe heteroduplex which reduces the $Tm_{bp}$ (as well as $Tm_{bt}$) relative to $Tm_{pt}$. Applicant has found that, under LCR conditions, a single base deletion is preferred and is sufficient to effect a 5°–8° C. difference in the Tm. In general, a Tm differential of 2°–20° C. is sufficient, preferably 3°–15° C. and optimally 5°–10° C. The blocking oligo:probe heteroduplexes are thus stable at lower storage temperatures (ambient or below) where masking is desired, but unstable at the warmer annealing temperatures used in PCR and LCR (typically 50°–70° C.) where interference is preferably avoided. This technique is illustrated in examples 1–2, 4–9 and 11–12. While applicant has found deletions to be preferred, additions and/or mismatches will have a similar impact on the Tm and may also be employed. One can then carry out the annealing and extension reactions under conditions (e.g. temperature) intermediate $Tm_{bt}$ and $tm_{pt}$ such that pp and pt homoduplexes form, but bp and bt heteroduplexes do not form in substantial amounts.

Two applications of this interference control technique are particularly useful when all four probes are blocked in LCR. It will be recalled in this case $Tm_{bb}$ must>$Tm_{bp}$. In a first variation, depicted in FIG. 4, a tail or extension is added to the blocking oligo. The tails of such blocking oligos should be relatively long and complementary to each other but not to the target. In this technique; the Tm of the blocking oligo homoduplex ("$Tm_{bb}$"), is increased and stabilizes the bb homoduplexes preferentially over the bt or bp heteroduplexes, thereby "sequestering" the blocking oligos.

Such tails may be characterized as (I)n and (I')n on the one side, and (J)m and (J')m on the other side and should not be complementary to the target DNA. (I)n and (J)n are, for example, polynucleotide sequences having from 2 to about 100 nucleotides; typically 2 to 50, more typically 5–10. (I)n and (J)m may be homopolymeric, or heteropolymeric wherein each occurrence of I and J is independently determined. The length (n) of the I extension and the length (m) of the J extension may be the same or different. Also, I and I' may be the same length (as may J and J'). (I')n and (J')m represent polynucleotide sequences complementary to (I)n and (J)m, respectively. While there is no advantage to be gained by varying the length of (I)n relative to (I')n (because only paired bases contribute to Tm) such variance is within the invention.

Another variation of the sequestration technique, shown in FIG. 6, employs covalent means for coupling the two blocking oligos in the blocking oligo homoduplex. This is a more permanent prevention of the blocking probe from interfering since it does not rely on just the stability of the hydrogen bonds of the paired strands. Thus, while tails may be preferable to promote the alignment and initial annealing of blocking oligo homoduplexes, they at least may be shorter, for example, from 5 to 50 nucleotides. The mechanism of this technique is to crosslink or otherwise covalently tie the blocking oligos to one another to permanently remove them from interfering. For example as shown in FIG. 6, an upstream probe is blocked with a blocking oligo having a hairpin-forming 5' nucleotide extension with a reactive coupling moiety at its 5' terminus. The complementary downstream probe is blocked with an oligo having a 3' reactive coupling moiety. The upstream probe, the downstream probe and the oligo blocking the downstream probe are all essentially coterminal at the external ends. The hairpin end of the upstream probe's blocking oligo terminates with little or no gap between it and the probe it masks. This configuration permits the blocking oligos, when separated from their probes, to anneal such that the reactive coupling groups are adjacent one another to facilitate activation and covalent attachment.

Several methods for covalent coupling of oligonucleotides are known in the art. For example, EP-A-0 324 616 (Amoco) and WO 90/01069 (Segev) both describe numerous compounds which can be attached to oligonucleotides and which are known to form covalent linkages upon exposure to light energy. The disclosure of these documents is incorporated by reference. Illustrative compounds are coumarins, psoralens, anthracenes, pyrenes, carotenes, tropones, chromones, quinones, maleic anhydride, alkyl maleidmide, olefins, ketones and azides. Methods for making the above compounds and for coupling them to oligonucleotides are taught in the prior art. In a variation of this, chemical groups that can be coupled together may be used in place of photoactivatable groups. Such groups are described for the purpose of joining oligonucleotides in WO 94/29485 (Segev), which is also incorporated by reference.

Such chemical and photochemical couplings can be arranged between reactive groups on complementary probes or on adjacent probes. Thus, complementary probes of a probe set (i.e. both upstram and downstream probes) may be masked utilizing complementary blocking oligos having a reactive chemical group on the 5' end of one oligo and on the 3' end of the other oligo. Depending on the orientation, these ends may be internal, wherein the chemical groups may serve also to mask the respective probes (see above); or they may be external (i.e. distal to the point of ligation); or both. Either way, the ends of the blocking oligos in the blocking oligo homoduplex can be sufficiently close to place these reactive groups in position to be covalently coupled upon the triggering event, be it light energy or chemical activation. The blocking oligos are thus covalently coupled and are permanently removed from interfering with the amplification reaction.

Yet another variation of Tm interference control is useful in the embodiment where a single blocking oligo spans the gap between two probes as shown in FIG. 5. In this configuration, the blocking oligos are designed to hybridize with target probes over only about half their length but, upon separation, the blocking oligos can hybridize with each other over approximately their entire length. This maximizes the Tm of the bb homoduplex while reducing the Tm of the bp heteroduplex, resulting in a $tm_{pt}$ that exceeds $Tm_{bp}$. In this case however, the $Tm_{bb}$ is approximately equal the $Tm_{bt}$.

In all cases, the masked probe duplexes must be stored under conditions that avoid premature unmasking. For most embodiments, this merely means storage at reduced temperatures. A drawback of the covalent coupling group techniques is that storage conditions may also require shielding from light or other triggering stimuli.

Figure 7:
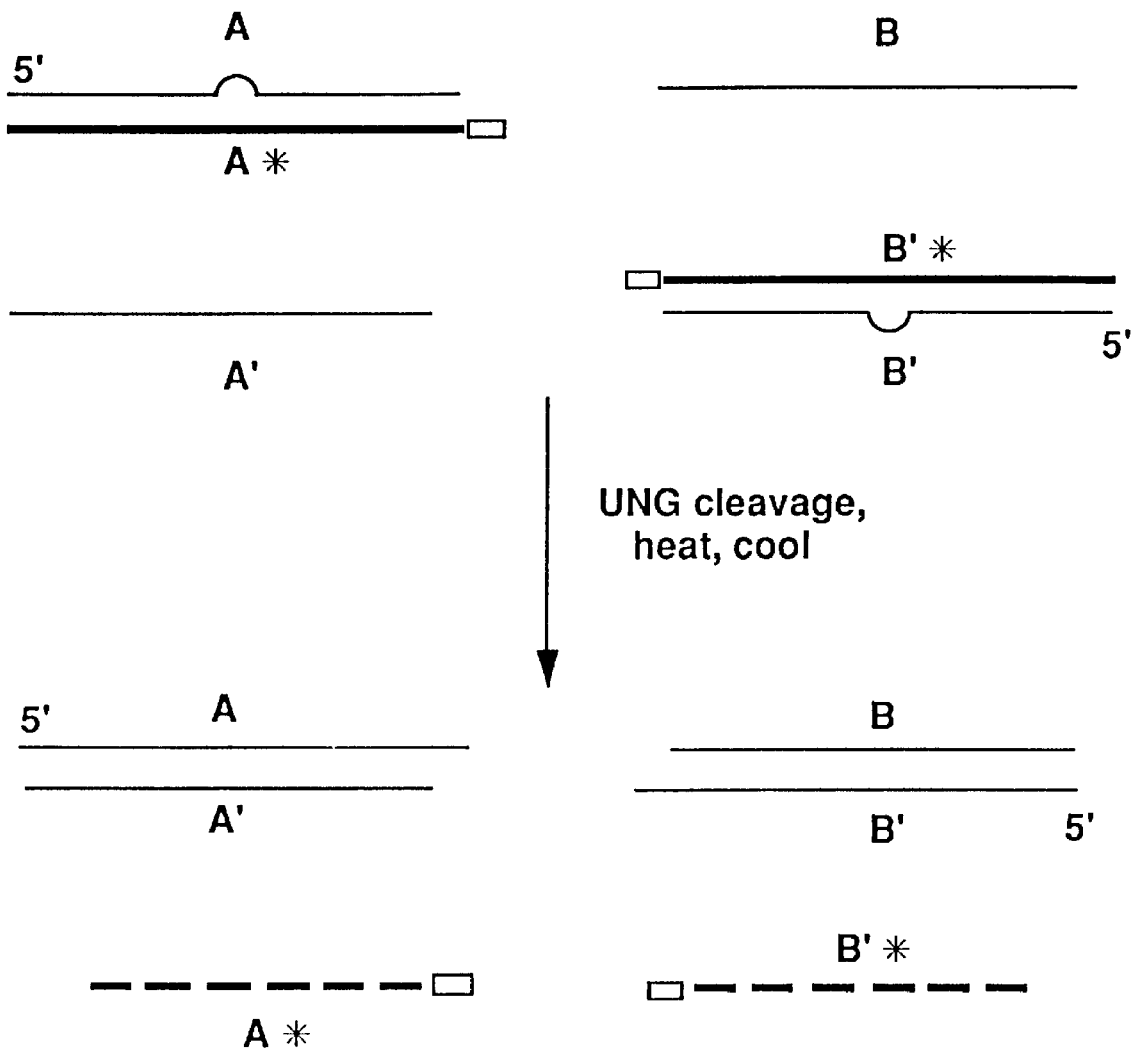
FIG. 7 is a schematic representation of another embodiment of the invention using two 5' stopbase blocking oligos (A* and B'*) which hybridize to the upstream LCR probes. This embodiment is like that of FIG. 2, except the deletion "bubble" may or may not be present. In this embodiment interference control is provided by degrading the blocking oligo after initiation of amplification.
Figure 8:
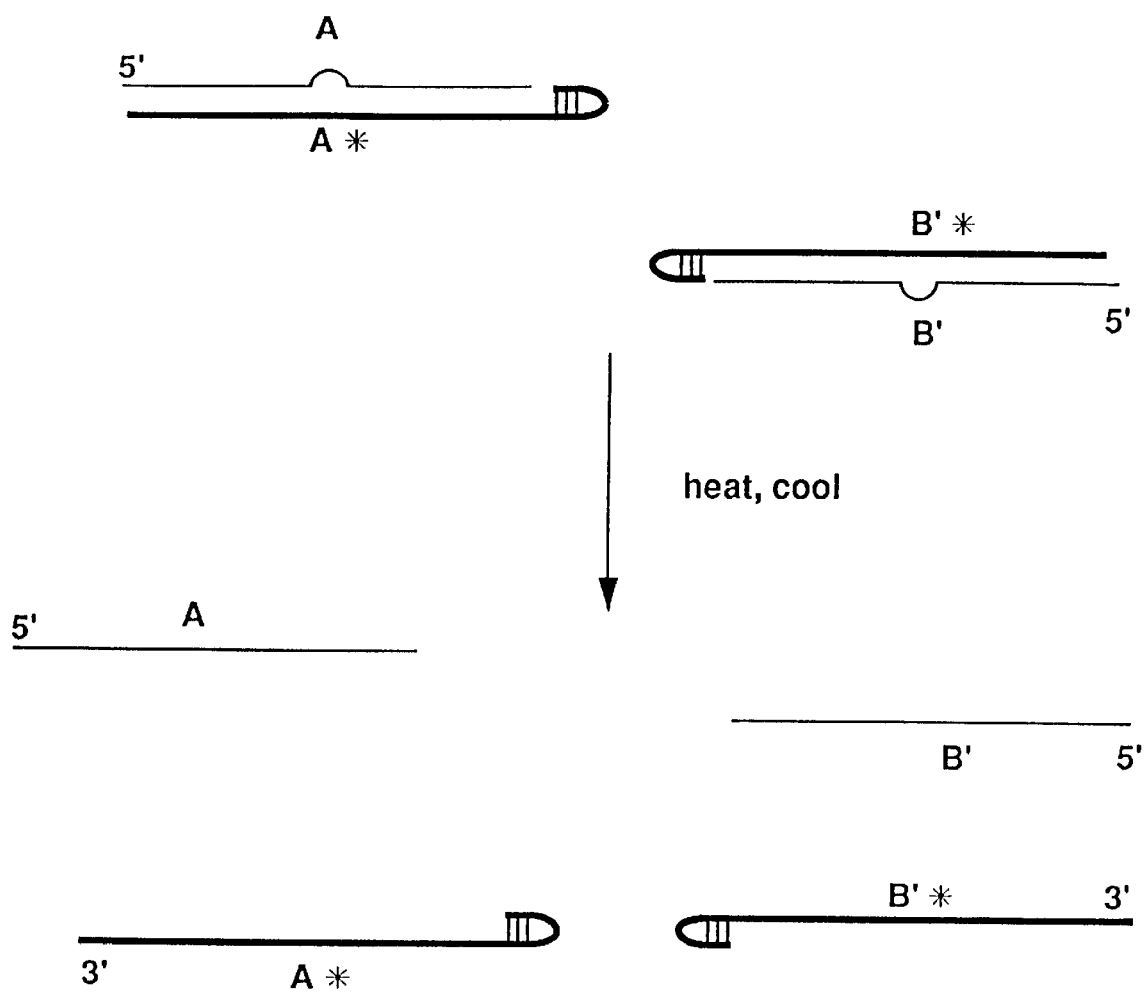
FIG. 8 is a schematic representation of another embodiment of the invention using two 5' hairpin blocking oligos (A* and B'*) which hybridize to a pair of PCR primers. This embodiment is like that of FIG. 1, except there can generally be no stopbase in PCR extensions so the hairpin alone must block. Crosslinking in the hinge region of the hairpin may be desired to "lock" the bend and prevent unfolding and inadvertent extension using the blocking oligo as template. Interference control is provided by a deletion, depicted by the bubble in the probe, which makes the probe:oligo heteroduplex less stable than the probe:target homoduplexes.

The second type of interference control involves the degradation of the blocking oligo once amplification begins. Degradation may be chemical or enzymatic or both, provided it acts substantially only on blocking oligos and only after amplification has begun. For example as shown in FIG. 7, blocking oligos may include dU in place of dT. Then deoxyuracil N glycosylase ("dUNG") can remove the uracil bases, which is followed by cleavage at the resultant abasic sites under thermal cycling conditions.

It is also possible to use combinations of the above probe masking techniques and/or interference avoidance techniques. If desired one might use a hairpin extension/stop base blocking oligo for one amplification probe, while using a hapten or other blocking moiety on a different amplification probe. Similarly, one might destabilize the blocking oligo:target probe duplex on one side by the introduction of bubble causing deletions or additions, while employing a sequestration technique to remove interference of the blocking oligos on the other side.

D. REAGENTS AND MATERIALS

The polymerases and ligases useful for this invention are commercially available. They should generally be thermostable for PCR and LCR reactions that undergo thermal cycling. Thermostable polymerases are available from Hoffmann-LaRoche/Perkin Elmer, Boehringer Mannheim and others. Amplitaq™ is a suitable thermostable polymerase. Thermostable ligases are also available from Epicentre (City, ST), New England Biolabs (City, Mass.), Stratagene (City, Calif.) and Molecular Biology Resources (Milwaukee, Wis.).

Synthesis of polynucleotides, whether amplification probes or blocking oligos, is now automated and routine. Labeling of the amplification probes with suitable haptens was described above. Attachment of coupling blocking moieties is described in the prior art, including the applications referenced above.

E. DETECTION

Detection of amplification products is performed by any suitable means. A preferred method of detection is the use of microparticle capture enzyme immunoassays (MEIA) for the detection of the amplification products. MEIA is described by Fiore, et al, *Clin. Chem.* 34(9): 1726–1732 (1988) and in EP-A-288 793, and a commercial clinical analyzer that utilizes this method is the IMx® instrument, marketed by Abbott Laboratories (Abbott Park, Ill.). For MEIA detection of amplification products, both capture haptens (hapten1) and detection haptens (hapten2) must be associated (e.g. covalently attached to) each amplification product. This is distinct from the use of haptens as blocking moieties in the masking reactions. The incorporation of haptens into LCR or PCR reaction products is known in the art, for example from EP-A-0 357 011 and EP-A-0 439 182. Briefly, the method employs primers (in a PCR reaction) which have reactive pair members linked to them. The reactive pair members can be attached to a solid phase and/or detected by labeled conjugates. Reactive pairs were selected from the group of hapten and antibody, biotin and avidin, enzyme and enzyme receptor, carbohydrate and lectin, and pairs of complementary DNA strands.

F. COMPOSITIONS AND KITS

Compositions come in multiple configurations depending on the amplification reaction (PCR or GLCR) and on the number and type of blocking oligos (see above). A typical PCR kit will include the two amplification primers each of which has been masked with a blocking oligo of one type or another. A typical LCR kit includes four amplification probes. Preferably all four are masked, but only two may be. Preferably the probes are reacted with the blocking oligos in separate reactions to ensure effective masking. The masked probes may then be mixed together, provided the reagent mixture is stored under conditions that discourage separation of the blocking oligos and reorganization of the amplification probes. Any permutation of masking means and interference control may be found in such compositions and kits.

In addition to the masked probe reagent compositions, kits will generally include the necessary enzymes, typically a thermostable polymerase and/or ligase; cofactors such as magnesium and NAD; suitable buffers or buffered solutions; and detection means for interpreting a result. Detection means may include, for example, antibody conjugates, enzymes and substrates or indicators, solid phases and the like.

EXAMPLES

The invention will now be described further by way of examples. The examples are illustrative of the invention and are not intended to limit it in any way. Throughout the examples the following abbreviations have the meanings given.

Adamantane, when used in the context of a reporter hapten, means the immunogenic 3-phenyl-1-adamantaneacetic acid compound described in the examples of co-pending application Ser. No. 08/049,888, which is incorporated by reference.

Carbazole, when used in the context of a reporter hapten, means the immunogenic carbazole compound described in the examples of co-pending application Ser. No. 08/084,495 which is incorporated by reference.

IFU refers to one inclusion forming unit which is theoretically equivalent to one organism. Because Chlamydia is an obligate intracellular parasite, it is difficult to quantify control dilutions with accuracy. Control solution IFUs are estimated by their IMx® rate using a standard curve calibrated against stock solutions cultured out to estimate IFUs.

LCR buffer is 50 mM EPPS pH7.8, 20 mM KC1 and 30 mM $MgCl_2$

Oligo refers generally to an oligodeoxyribonucleotide but may, as context permits, refer to an oligoribonucleotide.

Units of enzyme: A unit of polymerase is defined according to the manufacturer, Molecular Biology Resources, Milwaukee, Wis. A unit of ligase is defined as: 1 mg of 95% purified *Thermus thermophilus* DNA ligase has a specific activity of about $1 \times 10^8$ units; While this is not precisely standardized and may vary by as muc h as 20%, optimization is within the skill of the routine practitioner.

Examples 1–4

Chlamydia LCR with blocking oligos

The following double-stranded target DNA sequence (SEQ ID No. 5) is presented as only a single strand for simplicity sake. The target corresponds to map positions 435–482 of the *Chlamydia trachomatis* MOMP gene; per Zhang, Y. -X., Morrison, S. G., and Caldwell, H. D. Nucleic Acids Research 18:1061 (1990).

5' . . . GCTTTGAGTTCTGCTTCCTCCTTG-CAAGCTCTGCCTGTGGGGAATCCT . . . 3' (SEQ. ID No:5)5

The following target-specific probes (also referred to herein as "amplification probes") and blocking oligos were designed to detect the above target sequence by LCR, with reduced background levels.

The probes specific for amplification of the target are shown below. The amplification probe set features two probes (SEQ ID Nos. 1 and 2) haptenated with carbazole (designated "D") and two probes (SEQ ID Nos. 3 and 4) haptenated with adamantane (designated "E"). Probes 1 and 3 are designed to match the target strand (SEQ ID No. 5); and thereby hybridize with the target's complement, while probes 2 and 4 are complementary and hybridize with the target strand shown. Probes 1 and 2 hybridize to each other, as do probes 3 and 4 as shown below.

Interference of the blocking oligo in amplification is minimized by having the Tm of the pt homoduplex be higher than the Tm of the bp and bt heteroduplexes. In this example, the Tm's of the target-specific probe homoduplexes ($Tm_{pt}$) range from 70° C.–72° C. and the Tm's of the blocking oligo heteroduplexes ($Tm_{bp}$) range from 63° C.–69° C. The heteroduplex Tm's of the blocking oligos are reduced in this example by deleting 1 nucleotide in the blocking oligos. The 5'-extensions of oligos 1* (SEQ ID No. 6) and 4* (SEQ ID No. 9) are non-complementary to the target so that the Tm of the oligo:target duplex is not affected.

Gap LCR was performed with and without blocking oligos. For the blocking oligo evaluation, $1 \times 10^{12}$ molecules

| Probe No. | | SEQ ID. No. |
|---|---|---|
|  | 5' .GCTTTGAGTTCTGCTTCCTCCTTGCAAGCTCTGCCTGTGGGGAATCCT..3' | 5 |
| 1 | 5' DGCTTTGAGTTCTGCTTCCTCCTTG | 1 |
| 2 | 3' DCGAAACTCAAGACGAAGGAGGp | 2 |
| 3 | pGCTCTGCCTGTGGGGAATCCTE 3' | 3 |
| 4 | GTTCGAGACGGACACCCCTTAGGAE 5' | 4 |

Example 1

Four blocking oligos; hairpin modified 5' ends

Blocking oligos were designed to be complementary to the target LCR probes above. The blocking oligos and their hybridization orientation is shown below.

each of target-specific probes 1 (SEQ ID No. 1) and 4 (SEQ ID No. 4) and $2 \times 10^{12}$ molecules each of blocking oligos 1* (SEQ ID No. 6) and 4* (SEQ ID No. 9) were mixed in a final volume of 20 μl LCR buffer ("LCR buffer" contains 50 mM EPPS pH7.8, 20 mM KCl and 30 mM $MgCl_2$). In a separate reaction tube, $1 \times 10^{12}$ molecules each of target-specific

| Probe No. | | SEQ ID. No. |
|---|---|---|
|  | 5' .GCTTTGAGTTCTGCTTCCTCCTTGCAAGCTCTGCCTGTGGGGAATCCT..3' | 5 |
| 1 | 5' DGCTTTGAGTTCTGCTTCCTCCTTG | 1 |
| 1* | 3' pCGAAACTCAA—ACGAAGGAGGAAC<u>CCGGTTTTTCCGG</u> | 6 |
| 2 | 3' DCGAAACTCAAGACGAAGGAGGp | 2 |
| 2* | 5'   GCTTTGAGTT—TGCTTCCTCCp | 7 |
| 3 | pGCTCTGCCTGTGGGGAATCCTE 3' | 3 |
| 3* | pCGAGACGGAC—CCCCTTAGGA    5' | 8 |
| 4 | GTTCGAGACGGACACCCCTTAGGAE 5' | 4 |
| 4* | <u>GGCCTTTTTGGCCC</u>AAGCTCTGCCTG—GGGGAAp      3' | 9 |

Each blocking oligo of the set has a terminal 3' phosphate blocking group to prevent extension. Here, and throughout these examples, dashes ("-") in a blocking oligo represent nucleotides which were deleted to affect Tm as described herein for interference control.

Throughout this application, the asterisk ("*") designation is used to denote a blocking oligo corresponding to the amplification probe. For example, blocking oligo 1* (SEQ ID No. 6) is complementary to amplification probe 1 (SEQ ID No. 1); blocking oligo 2* (SEQ ID No. 7) is complementary to amplification probe 2 (SEQ ID No. 2); blocking oligo 3* (SEQ ID No. 8) is complementary to amplification probe 3 (SEQ ID No. 3); and blocking oligo 4* (SEQ ID No. 9) is complementary to amplification probe 4 (SEQ ID No. 4). The underlined sequences (5'-extension) in probes 1* (SEQ ID No. 6) and 4* (SEQ ID No. 9) have the potential to form a hairpin loop structure, even when hybridized to their complementary target-specific probes. This underlining convention is used in this manner throughout the examples. When a target-specific probe is hybridized to its complementary blocking oligo, 5' to 3' extension of the target-specific probe by DNA polymerase is prohibited by the potential secondary structure and/or by the presence of stop bases (C) in the 5' extensions of oligos 1* (SEQ ID No. 6) and 4* (SEQ ID No. 9).

probes 2 (SEQ ID No. 2) and 3 (SEQ ID No. 3) and $2 \times 10^{12}$ molecules each of blocking oligos 2* (SEQ ID No. 7) and 3* (SEQ ID No. 8) were mixed in a final volume of 20 μl LCR buffer containing 50 mM EPPS pH7.8, 20 mM KCl and 30 mM $MgCl_2$. Both mixtures were heated to 100° C. and then slow cooled to room temperature. The resulting blocked-probe mixtures were combined and added to a reaction mix containing LCR buffer, 100 μM NAD, 1 μM 2'-deoxyadenosine 5'-triphosphate (dATP) and 1 μM 2'-deoxycytosine 5'-triphosphate (dCTP).

Next, 0 or 2.5 IFUs of *Chlamydia trachomatis* genomic DNA (containing the MOMP gene target), 330 nanograms of human placental DNA and an enzyme mix containing 50 mM EPPS pH7.8, 20 mM KCl, 30 mM $MgCl_2$, 10 μg/ml acetylated BSA, 10000 units *Thermus thermophilus* DNA ligase and 1 unit Taq DNA polymerase were added. The reaction tubes were incubated at room temperature for 1 hour. Gap LCR was then performed for 43 cycles, each cycle consisting of a 1 second incubation at 97° C., a 1 second incubation at 61° C. and a 50 second incubation at 68° C. using a Perkin-Elmer 480 thermocycler. In all cases, the final reaction volume was 100 μl and the reaction was overlaid with approximately 20 μl of mineral oil prior to cycling.

Gap LCR was also performed without blocking oligos to determine the amount of background with target-specific probes. This protocol differs slightly from the blocking oligo protocol described supra. One×10$^{12}$ molecules each of target-specific probes 1 (SEQ ID No. 1), 2 (SEQ ID No. 2), 3 (SEQ ID No. 3) and 4 (SEQ ID No. 4) were added to a reaction mix containing LCR buffer (described supra), 100 μM NAD, 1 μM (dATP) and 1 μM (dCTP). Next, 0 or 2.5 IFUs of target DNA (*Chlamydia trachomatis* genomic DNA), 330 nanograms of human placental DNA and an enzyme mix containing 50 mM EPPS pH 7.8, 20 mM KCl, 30 mM MgCl$_2$, 10 μg/ml acetylated BSA, 10000 units *Thermus thermophilus* DNA ligase and 1 unit Taq DNA polymerase were added. The final reaction volume was 100 μl. The reaction tubes were incubated at room temperature for 1 hour, and gap LCR was performed for 43 cycles as described supra.

Figure 9B:
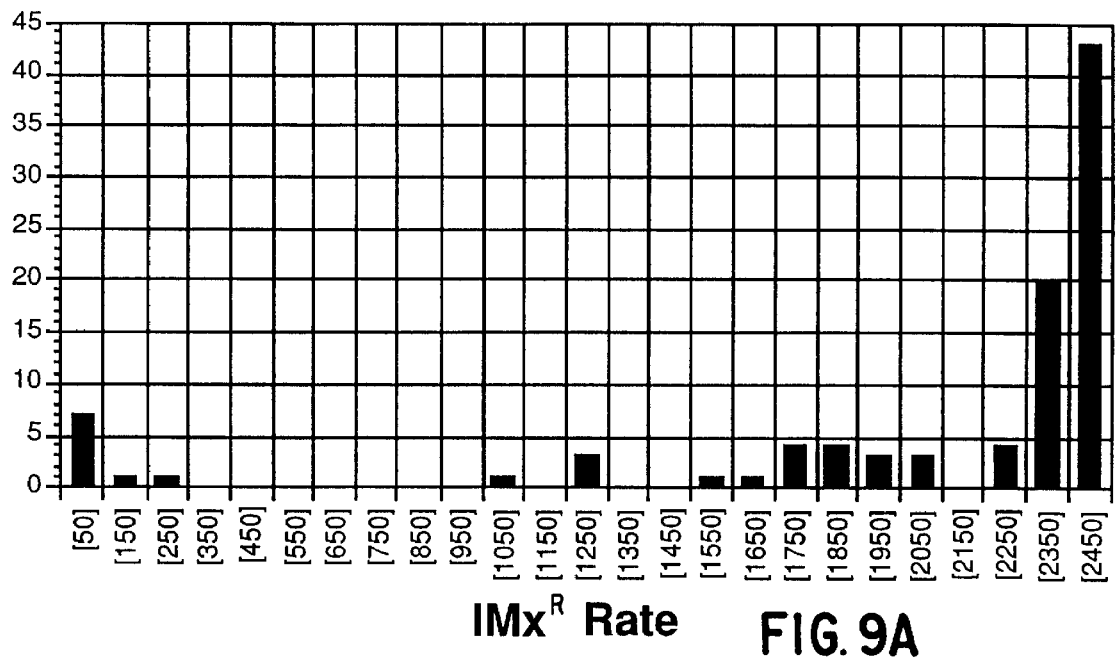
FIG. 9B is a representation of the rate range when blocking oligos were added. The y axis shows the number of samples of a particular rate.
Figure 9B:
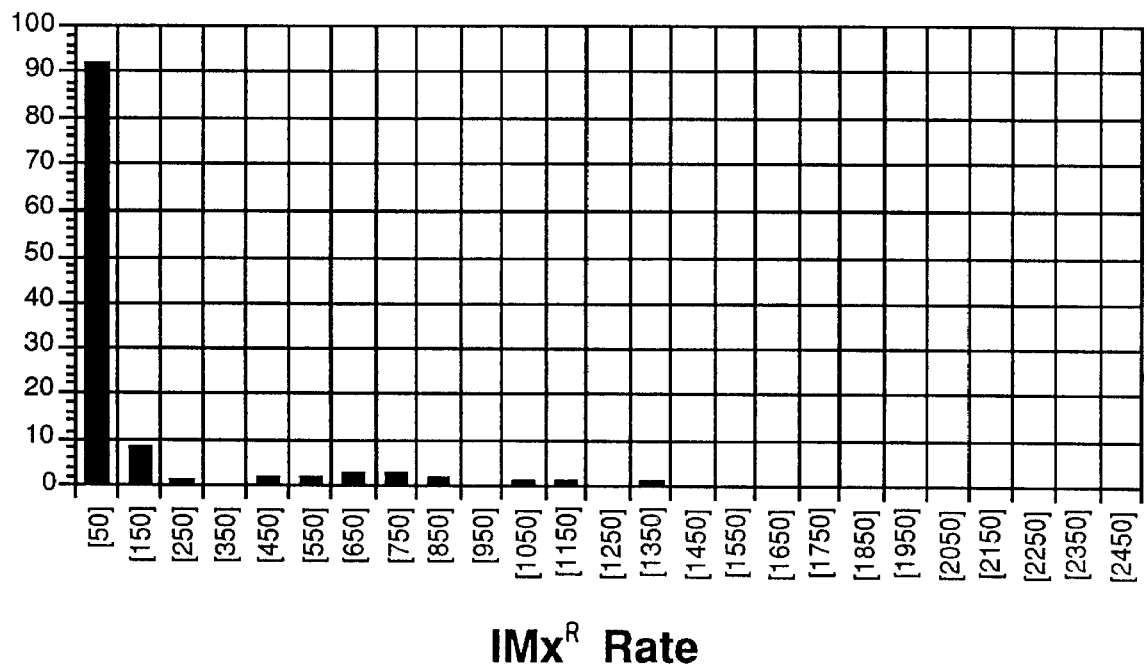

Following amplification, the carbazole-adamantane LCR amplification products were detected via a sandwich immunoassay performed on the Abbott IMx® Microparticle Enzyme Immunoassay ("MEIA") system. The reduction of background using blocking oligos is demonstrated in Table 1A and in FIG. 9 for samples lacking target DNA. In Table 1B, samples containing target DNA were amplified with target-specific probes with and without blocking oligos. The data show that the blocking oligos have a negligible effect on the efficiency of amplification. Negative reactions should typically give rates of ≦100 c/s/s.

TABLE 1A

| Rate Range (c/s/s) | No Target No Blocking | No Target + Blocking |
|---|---|---|
| 0–100 | 7 | 92 |
| 100–200 | 1 | 8 |
| 200–300 | 1 | 1 |
| 400–500 | 0 | 2 |
| 500–600 | 0 | 2 |
| 600–700 | 0 | 3 |
| 700–800 | 0 | 3 |
| 800–900 | 0 | 2 |
| 1000–1100 | 1 | 1 |
| 1100–1200 | 0 | 1 |
| 1200–1300 | 3 | 0 |
| 1300–1400 | 0 | 1 |
| 1500–1600 | 1 | 0 |
| 1600–1700 | 1 | 0 |
| 1700–1800 | 4 | 0 |
| 1800–1900 | 4 | 0 |
| 1900–2000 | 3 | 0 |
| 2000–2100 | 3 | 0 |
| 2200–2300 | 4 | 0 |
| 2300–2400 | 20 | 0 |
| 2400–2500 | 43 | 0 |
| Total | 96 | 116 |

TABLE 1B

| No of Samples | 2.5 IFUs Target No Blocking Rates (c/s/s) | 2.5 IFUs Target + Blocking Rates (c/s/s) |
|---|---|---|
| 6 | 1785 ± 184 | 1513 ± 123 |

Example 2

Four blocking oligos; PNA modified 5' ends

The Gap LCR amplifications and IMx® detections of example 1 are repeated except the following blocking oligo set (5*, 2*, 3* and 6*; SEQ ID Nos. 10, 7, 8 and 11) is used with the target-specific probe set of example 1 (SEQ ID Nos 1, 2, 3 and 4) to amplify target DNA.

| Probe No. | | SEQ ID. No. |
|---|---|---|
| | 5'..GCTTTGAGTTCTGCTTCCTCCTTGCAAGCTCTGCCTGTGGGGAATCCT..3' | 5 |
| 1 | 5' DGCTTTGAGTTCTGCTTCCTCCTTG | 1 |
| 5* | 3' pCGAAACTCAA—ACGAAGGAGGAAC<u>F</u> | 10 |
| 2 | 3' DCGAAACTCAAGACGAAGGAGGp | 2 |
| 2* | 5'  GCTTTGAGTT-TGCTTCCTCCp | 7 |
| 3 | PGCTCTGCCTGTGGGGAATCCTE 3' | 3 |
| 3* | PCGAGACGGAC-CCCCTTAGGA  5' | 8 |
| 4 | GTTCGAGACGGACACCCCTTAGGAE 5' | 4 |
| 6* | <u>F</u>CAAGCTCTGCCTG—GGGGAAp     3' | 11 |

The nucleotide sequence of the blocking oligos is the same as in example 1, except the 5'-ends of the blocking oligos 5* (SEQ ID No. 10) and 6* (SEQ ID No. 11), (which are used in place of oligos 1* (SEQ ID No. 6) and 4* (SEQ ID No. 9), contain F, a 3 base extension ("CCC") of peptide bond linked nucleotides (double underlined) instead of the 5' hairpin extension and stopbase. The sequence of the extension is not material, and one need not be concerned with a stopbase, since such PNAs do not act as a template for the 5' to 3' extension of the target-specific LCR probe.

Chimeric DNA/PNA molecules are synthesized by performing the PNA synthesis reactions as disclosed in WO 93/25706 using the protected basic oligonucleotide sequence as starting material.

As in example 1, the blocking oligos contain terminal 3' phosphates to prevent extension. The Tm of the blocking oligo:amplification probe hybrid is reduced by deleting the dashed nucleotide. When a target-specific probe is hybridized to its complementary blocking oligo, 5' to 3' extension by DNA polymerase of the target-specific probe is prohibited.

Example 3

Four blocking oligos; "tailed" Tm control

The following blocking oligo set is used with the target-specific probe set of example 1 to amplify the target DNA.

| Probe No. | | SEQ ID. No. |
|---|---|---|
| | 5'..GCTTTGAGTTCTGCTTCCTCCTTGCAAGCTCTGCCTGTGGGGAATCCT..3' | 5 |
| 1 | 5' DGCTTTGAGTTCTGCTTCCTCCTTG | 1 |
| 7* | 3' p(I)nCGAAACTCAA—ACGAAGGAGGAACF | 12 |
| 2 | 3' DCGAAACTCAAGACGAAGGAGGp | 2 |
| 8* | 5' (I')nGCTTTGAGTT—TGCTTCCTCCp | 13 |
| 3 | pGCTCTGCCTGTGGGGAATCCTE 3' | 3 |
| 9* | pCGAGACGGAC-CCCCTTAGGA(J)m 5' | 14 |
| 4 | GTTCGAGACGGACACCCCTTAGGAE 5' | 4 |
| 10* | FCAAGCTCTGCCTG—GGGGAATCCT(J')mp3' | 15 |

The nucleotide sequence of the blocking oligos 7*, 8*, 9* and 10* are the same as for blocking oligos 5*, 2*, 3* and 6*, respectively, in example 2, except for F and the following nucleotide extensions. Probe 7* (SEQ ID No. 12) contains a 3' nucleotide extension of 10 bases, (I)n, which is complementary to a 5' nucleotide extension, (I')n, of probe 8* (SEQ ID No. 13). Similarly, probe 9* (SEQ ID No. 14) contains a 5' nucleotide extension of about 10 bases, (J)m, which is complementary to a 3' extension, (J')m, of probe 10* (SEQ ID No. 15). F in this example represents a 5' hairpin structure with stopbase as in example 1.

In this example interference of the blocking oligos is further minimized by ensuring that homoduplex hybrids composed of two complementary blocking oligos have a higher Tm than probe:blocking oligo heteroduplexes, preferably even higher than that of probe:target homoduplexes (i.e. $Tm_{bb} > Tm_{pb}$), whereby the blocking oligos bind to each other forming stable hybrids and are less likely to compete with the target-specific probes in the LCR reaction.

The gap LCR amplification and IMx® detection are repeated as in example 1 using instead the above-described blocking oligo set.

Example 4

Two blocking oligos (1 & 4 with 5' mismatches)

The following blocking oligos are used with the target-specific probe set of example 1 to amplify the target DNA.

blocking oligos 1* (SEQ ID No. 16) and 4* (SEQ ID No. 17); while probes 2 (SEQ ID No. 2) and 3 (SEQ ID No. 3) remain unblocked. In this example, the blocking oligo utilizes a 5' end mismatch (double underline) to prevent inadvertent extension of the amplification probe. The 3' end of each blocking oligo carries a phosphate to prevent extension, and the dash indicates a deleted base for Tm interference control as in example 1, although some reduction in $Tm_{bp}$ is achieved by the mismatches alone.

The gap LCR amplification and IMx® detection are repeated as in example 1 using instead the above-described blocking oligo set.

Examples 5–7

HBV LCR with blocking oligos

The following duplex target DNA sequence (SEQ ID No. 22) is presented as only a single strand for simplicity sake. It represents HBV DNA corresponding to map positions 231–279 of the HBV surface antigen gene (adr subtype); per Ono, Y. et al. Nucleic Acids Research 11: 1747–1757 (1983).

| Probe No. | | SEQ ID. No. |
|---|---|---|
| | 5'.GCTTTGAGTTCTGCTTCCTCCTTGCAAGCTCTGCCTGTGGGGAATCCT..3' | 5 |
| 1 | 5' DGCTTTGAGTTCTGCTTCCTCCTTG | 1 |
| 1* | 3' pCGAAACTCAA—ACGAAGGAGG<u>ATT</u> | 16 |
| 2 | 3' DCGAAACTCAAGACGAAGGAGGp | 2 |
| 3 | pGCTCTGCCTGTGGGGAATCCTE 3' | 3 |
| 4 | GTTCGAGACGGACACCCCTTAGGAE 5' | 4 |
| 4* | <u>TT</u>AGCTCTGCCTG—GGGGAAP 3' | 17 |

In this example, target specific amplification probes 1 (SEQ ID No. 1) and 4 (SEQ ID No. 4) are blocked by

| Probe No. | | SEQ ID. No. |
|---|---|---|
| | 5'...CCTCACAATACCACAGAGTCTAGACTCGTGGTGGACTTCTCTCAATTTT...3' | 22 |
| 11 | 5' DCCTCACAATACCGCAGAGTCTAGA | 18 |
| 12 | 3' DTTAGGAGTGTTATGGCGTCTCAGAp | 19 |
| 13 | pGTGGTGGACTTCTCTCAATTTTCTE 3' | 20 |
| 14 | GAGCACCACCTGAAGAGAGTTAAAAGE 5' | 21 |

The amplification probe set features two target-specific probes (11 & 12; SEQ ID Nos. 18 and 19) haptenated with carbazole (designated "D") and two target-specific probes (13 & 14; SEQ ID Nos. 20 and 21) haptenated with adamantane (designated "E"). Probes 11 and 13 (SEQ ID Nos. 18 and 20) are designed to match the target strand (SEQ ID No. 22); and thereby hybridize with the target's complement, while probes 12 and 14 (SEQ ID Nos. 19 and 21) are complementary and hybridize with the target strand shown. Probes 11 and 12 hybridize to each other, as do probes 13 and 14 as shown above. There is a single base mismatch, shown in italics, between target-specific probe 11 (SEQ ID No. 18) and the target DNA.

Example 5

Two blocking oligos (2 & 3 with 3' phosphate)

Target-specific amplification probes and blocking oligos (shown below) were designed to detect the above target sequence by LCR with reduced background levels.

placental DNA and an enzyme mix containing 50 mM EPPS pH7.8, 20 mM KCl, 30 mM $MgCl_2$, 10 μg/ml acetylated BSA, 10000 units *Thermus thermophilus* DNA ligase and 1 unit Taq DNA polymerase were added. The reaction tubes were incubated at room temperature for 2 hours. Gap LCR was then performed for 38 cycles, each cycle consisting of a 1 second incubation at 97° C., a 1 second incubation at 60° C. and a 50 second incubation at 67° C. using a Perkin-Elmer 480 thermocycler. In all cases, the final reaction volume was 100 μl and the reaction was overlaid with approximately 20 μl of mineral oil prior to cycling.

Gap LCR was also performed without blocking oligos to determine the amount of background with target-specific probes. This protocol differs slightly from the blocking oligo protocol described supra. Five×$10^{11}$ molecules each of target-specific probes 11 (SEQ ID No. 18), 12 (SEQ ID No. 19), 13 (SEQ ID No. 20) and 14 (SEQ ID No. 21) were added to a reaction mix containing LCR buffer (described in example 1), 100 μM NAD, 1 μM [dATP] and 1 μM [dGTP]. Next, 0 or 100 molecules of target DNA (Hepatitis B virus ADR subtype genomic DNA), 330 nanograms of human

| Probe No. | | | SEQ ID. No. |
|---|---|---|---|
| | 5'...CCTCACAATACCACAGAGTCTAGACTCGTGGTGGACTTCTCTCAATTTT...3' | | 22 |
| 11 | 5' | DCCTCACAATACCGCAGAGTCTAGA | 18 |
| 12 | 3' DTTAGGAGTGTTATGGCGTCTCAGAp | | 19 |
| 12* | 5' | CCTCACAATA—CGCAGAGTCTAGAp | 23 |
| 13 | | pGTGGTGGACTTCTCTCAATTTTCTE 3' | 20 |
| 13* | | pGAGCACCACCTGA—GAGAGTTAAAAG 5' | 24 |
| 14 | | GAGCACCACCTGAAGAGAGTTAAAAGE 5' | 21 |

The blocking oligos were designed to be complementary to the amplification probes. Each blocking oligo of the set has a terminal 3' phosphate to prevent extension. The dashes represent nucleotides which were deleted in the blocking oligos, to affect Tm as described herein. Blocking oligos 12* (SEQ ID No. 23) and 13* (SEQ ID No. 24) have 3' phosphorylated ends which prohibit their extension.

As in example 1, interference of the blocking oligo in amplification is minimized by having the Tm of probe:blocking oligo heteroduplexes be less stable than the probe:target duplexes. In this HBV example, the Tm's of the probe homoduplexes ($Tm_{pp}$ and $tm_{pt}$) range from 70° C.–71° C. The Tm's of the probe:blocking oligo heteroduplexes ($Tm_{pb}$) range from 64° C.–68° C.

In a first experiment, two blocking oligos 12* and 13* (SEQ ID Nos. 23 and 24) described above were used with the target-specific probe set (probes 11, 12, 13 and 14; i.e. SEQ ID Nos. 18, 19, 20 and 21) to amplify HBV target DNA with reduced background.

As in example 1, Gap LCR was performed both with and without blocking oligos. For the blocking oligo evaluation, 5×$10^{11}$ molecules each of target-specific probes 12 (SEQ ID No. 19) and 13 (SEQ ID No. 20) and 1×$10^{12}$ molecules each of blocking oligos 12* (SEQ ID No. 23) and 13* (SEQ ID No. 24) were mixed in a final volume of 20 μl LCR buffer containing 50 mM EPPS pH7.8, 20 mM KCl and 30 mM $MgCl_2$. The mixture was heated to 100° C. and then slow cooled to room temperature. This solution was then added to a reaction mix containing LCR buffer (described in example 1), 100 μM NAD, 1 μM [dTTP], 1 μM [dCTP]0 and 5×$10^{11}$ molecules each of LCR target-specific probes 11 (SEQ ID No. 18) and 14 (SEQ ID No. 21).

Next, 0 or 100 molecules of target DNA (Hepatitis B virus ADR subtype genomic DNA), 330 nanograms of human placental DNA and an enzyme mix containing 50 mM EPPS pH7.8, 20 mM KCl, 30 mM $MgCl_2$, 10 μg/ml acetylated BSA, 10000 units *Thermus thermophilus* DNA ligase and 1 unit Taq DNA polymerase were added. The final reaction volume was 100 μl. The reaction tubes were either incubated at room temperature for 2 hours, or amplified immediately for 38 cycles as described supra.

Following amplification, the carbazole-adamantane LCR amplification products were detected via a sandwich immunoassay performed on the Abbott IMx® system. As a control experiment, samples +/− target DNA and +/− preincubation were evaluated (Tables 5-A and 5-B). These data indicate that preincubation increases the background.

TABLE 5-A

| Target DNA | Rate (c/s/s) No Preincubation | Rate (c/s/s) + Preincubation |
|---|---|---|
| 100 molecules | 1252 | 1650 |

TABLE 5-B

| Samples (ID #) No Target DNA | Rates (c/s/s) No Preincubation | Rates (c/s/s) + Preincubation |
|---|---|---|
| 1 | 6 | 1621 |
| 2 | 29 | 1349 |
| 3 | 9 | 1533 |
| 4 | 9 | 1505 |
| 5 | 6 | 1472 |
| 6 | 17 | 1502 |
| 7 | 10 | 1546 |
| 8 | 7 | 717 |

Tables 5-C shows the effect of blocking oligos 12* (SEQ ID No. 23) and 13* (SEQ ID No. 24) on the amount of background observed for samples lacking target DNA. The effect of blocking oligos on the efficiency of amplification is shown in table 5-D. These data indicate that blocking oligos 12* (SEQ ID No. 23) and 13* (SEQ ID No. 24) reduce the background, but do not significantly impair the efficiency of amplification.

We observed that background was reduced by blocking oligos in this experiment even though the oligos blocked the downstream probes, rather than the upstream probes that are extended in Gap LCR. This suggests that the mechanism of background generation requires double stranded probes in order to generate the random tailing. It also illustrates the utility of this embodiment of the invention in that extension of upstream, extendable probes is en where only downstream probes are blocked.

TABLE 5-C

| Samples (ID #) No Target DNA | Rates (c/s/s) No Blocking Oligos | Rates (c/s/s) + Blocking Oligos |
|---|---|---|
| 1 | 1621 | 626 |
| 2 | 1349 | 588 |
| 3 | 1533 | 20 |
| 4 | 1505 | 621 |
| 5 | 4472 | 353 |
| 6 | 1502 | 199 |
| 7 | 1546 | 835 |
| 8 | 717 | 10 |

TABLE 5-D

| Target DNA | Rates (c/s/s) No Blocking Oligos | Rates (c/s/s) + Blocking Oligos |
|---|---|---|
| 100 molecules | 1650 | 1515 |

Example 6

Two blocking oligos (1 & 4 with 5' hairpin extension)

In another experiment, a different set of two blocking oligos, 11* (SEQ ID No. 25) and 14* (SEQ ID No. 26) was used with the target-specific probe set of example 5 (probes 11, 12, 13 and 14; i.e. SEQ ID Nos. 18, 19, 20 and 21) to amplify target DNA with reduced background.

In this example, target specific amplification probes 11 (SEQ ID No. 18) and 14 (SEQ ID No. 21) were blocked by blocking oligos 11* (SEQ ID No. 25) and 14* (SEQ ID No. 26); while probes 12 (SEQ ID No. 19) and 13 (SEQ ID No. 20) remain unblocked. In each case, the blocking oligo utilizes a hairpin-forming extension (underlined) and a 5' stopbase (C or T) to prevent extension of the upstream probe to which it hybridizes. The 3' end of each blocking oligo carries a phosphate to prevent extension.

The gap LCR amplification and IMx® detection are repeated as in example 5 using instead the above-described blocking oligo set.

Table 6-A shows the effect of blocking oligos 11* (SEQ ID No. 25) and 14* (SEQ ID No. 26) on the amount of background observed for samples lacking target DNA. The effect of blocking oligos on the efficiency of amplification is shown in table 6-B. These data indicate that blocking oligos 11* (SEQ ID No. 25) and 14* (SEQ ID No. 26) reduce the background, but do not significantly reduce the efficiency of amplification.

TABLE 6-A

| Samples (ID #) No Target DNA | Rates (c/s/s) No Blocking Oligos | Rates (c/s/s) + Blocking Oligos |
|---|---|---|
| 1 | 1621 | 12 |
| 2 | 1349 | 10 |
| 3 | 1533 | 8 |
| 4 | 1505 | 8 |
| 5 | 1472 | 14 |
| 6 | 1502 | 49 |
| 7 | 1546 | 11 |
| 8 | 717 | 13 |

TABLE 6-B

| Target DNA | Rates (c/s/s) No Blocking Oligos | Rates (c/s/s) + Blocking Oligos |
|---|---|---|
| 100 molecules | 1650 | 1264 |

Example 7

Two blocking oligos; across the gap junction

Example 5 is repeated but using the blocking oligos 11/13* and 12/14*, shown below, in place of the downstream probe blocking oligo set.

| Probe No. | | | SEQ ID. No. |
|---|---|---|---|
| | 5'...CCTCACAATACCACAGAGTCTAGACTCGTGGTGGACTTCTCTCAATTTT...3' | | 22 |
| 11 | 5'    DCCTCACAATACCGCAGAGTCTAGA | | 18 |
| 11* | 3'        pGGAGTGTTATG—CGTCTCAGATCT<u>CCGGTTTTCCGG</u> | | 25 |
| 12 | 3' DTTAGGAGTGTTATGGCGTCTCAGAp | | 19 |
| 13 | | pGTGGTGGACTTCTCTCAATTTTCTE 3' | 20 |
| 14 | | GAGCACCACCTGAAGAGAGTTAAAAGE    5' | 21 |
| 14* | | <u>AGGCCTTTTGGCCT</u>CTCGTGGTGGACT—CTCTCAATp    3' | 26 |

| Probe No. | | | | SEQ ID. No. |
|---|---|---|---|---|
| | | 5'...CCTCACAATACCACAGAGTCTAGACTCGTGGTGGACTTCTCTCAATTTTCT..3' | | 22 |
| 11/13 | 5' | DCCTCACAATACCGCAGAGTCTAGA    pGTGGTGGACTTCTCTCAATTTTCTE | 3' | 18/20 |
| 11/13* | 3' | pTCAGATCTTCTCACCACCT | 5' | 27 |
| 12/14 | 3' | DTTAGGAGTGTTATGGCGTCTCAGAp    GAGCACCACCTGAAGAGAGTTAAAAGE | 5' | 19/21 |
| 12/14* | 5' | AGTCTCTCCTCGTGGTGGAP | 3' | 28 |

Blocking oligo 11/13* (SEQ ID No. 27) is complementary to the 3' end of probe 11 (SEQ ID No. 18) and to the 5' end of probe 13 (SEQ ID No. 20). Blocking 12/14* (SEQ ID No. 28) is complementary to the 5' end of probe 12 (SEQ ID No. 19) and to the 3' end of probe 14 (SEQ ID No. 21). When a target-specific probe is hybridized to its complementary blocking oligo, 5' to 3' extension by DNA polymerase of the target-specific probe is prohibited by the presense of stop bases in the blocking oligos. For example, the C's and T's in the gap between the probes effectively serve as stopbases because the reaction mixture will contain neither dATP nor dGTP. The blocking oligos also contain terminal 3' phosphate groups to prevent DNA polymerase extension of the blocking oligos.

In this example, the blocking oligos 11/13* (SEQ ID No. 27) and/or 12/14* (SEQ ID No. 28) are preincubated with the target-specific probes 11–14 (SEQ ID Nos. 18, 19, 20 and 21). If both blocking oligos are used, however, they should be incubated separately with their corresponding target-specific probes and then combined for amplification as described in examples 5 and 6. Interference in the amplification reaction is minimized by manipulating the Tm of the blocking oligo:target-specific probe hybrids as described herein. For example, the $Tm_{bp}$ for a blocking oligo on either probe will be less than the $Tm_{pt}$ of both probes on the target and, while $Tm_{bb} \approx Tm_{bt}$ in this embodiment, both are still less than $Tm_{pt}$.

Following amplification, the carbazole-adamantane LCR amplification products may be detected via a sandwich immunoassay performed on the Abbott IMx® MEIA system.

Example 8

Tailing activity of DNA polymerase

Clark, *Nucl. Acids Res.*, 16(20):9677–9686 (1988) describes a target independent tailing activity associated with Taq polymerase ("Taq")wherein the polymerase is able to extend the 3' end of a blunt end DNA duplex using any of the 4 deoxyribonucleotide triphosphates. We examined the ability of Taq to extend both blunt duplexes and duplexes containing 1 base 3' overhang using the oligonucleotides shown below:

| Probe No. | | SEQ ID. No. |
|---|---|---|
| 15 | 3'-TGTATAAGTAGGCACGAATGTTGAA*-5' | 29 |
| 16 | 5'-ACATATTCATCCGTGCTTACAACT-3' | 30 |
| 17 | 5'-  CATATTCATCCGTGCTTACAACT-3' | 31 |

Oligonucleotide 15 (SEQ ID No. 29) was labeled ("*") at the 5' end using $\gamma$-$^{32}$P-ATP and polynucleotide kinase. Extension reactions contained 332 nM of either blunt duplexes (oligonucleotides 15 and 16; i.e. SEQ ID Nos. 29 and 30) or duplexes with a 1 base 3' overhang (oligonucleotides 15 and 17; i.e. SEQ ID Nos. 29 and 31) in 1x PCR buffer (Perkin-Elmer Corp). supplemented with 2.5 mM $MgCl_2$, 400 mM dNTP and 2.5 units Taq polymerase). Reaction volume was 5 μl. Each reaction was incubated at 55° C. for 30 minutes. Reactions were then mixed with an equal volume of formamide loading buffer and 5 μl was analyzed on a 15% acrylamide/8M urea gel.

Figure 10:
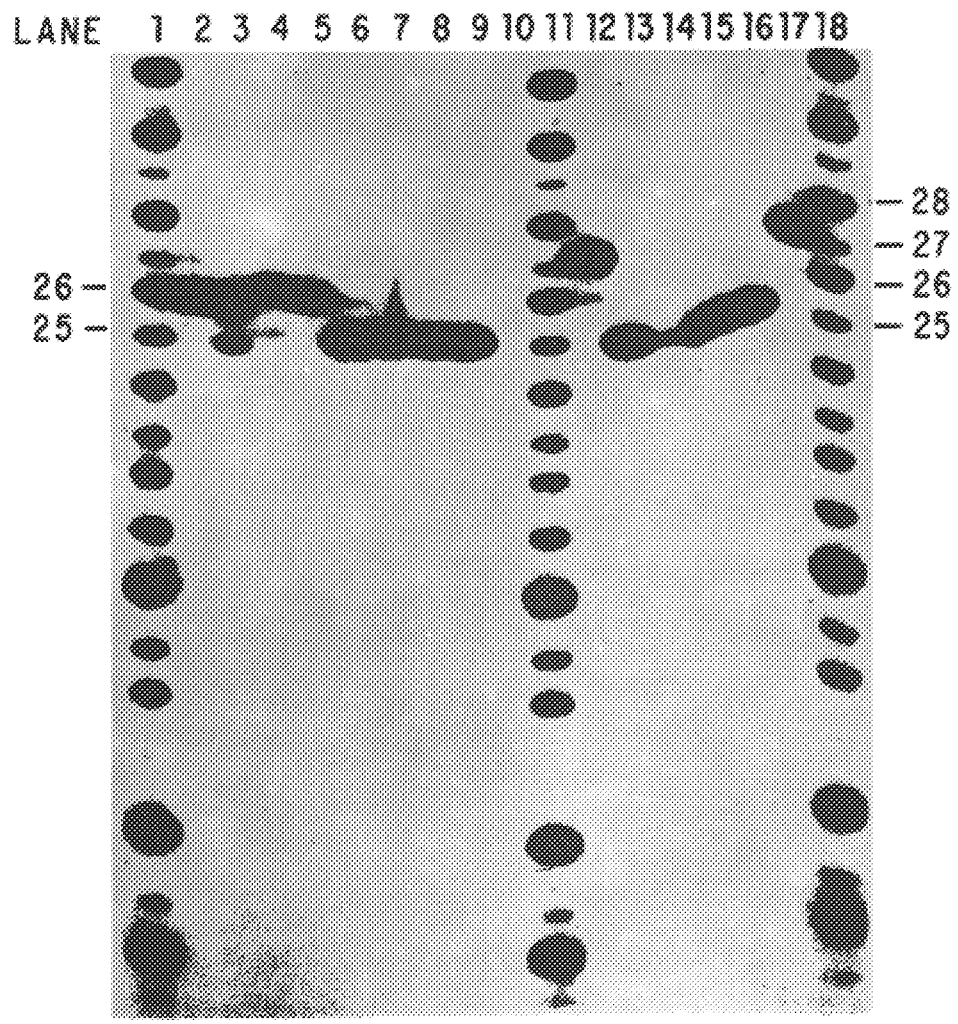
FIG. 10 is a print of an autoradiograph described in detail in Example 8. Lanes are numbered 1 to 18 across the top and the sides are marked with selected size markers run in lanes 1, 11 and 18. Other details are found in the example.

The results are shown in FIG. 10. Lanes 1, 11 and 18 are size markers. Lanes 2–5 demonstrate the ability of Taq to extend the 3' end of a blunt end duplex (oligonucleotide 15 (SEQ ID No. 29) extended from 25 to 26 nt) using each dNTP. A faint band representing a +2 addition product can be observed using dATP. Lanes 6–9 demonstrate the reduced ability of Taq to add nucleotides to duplexes containing a 1 base 3' overhang: (oligonucleotide 15 (SEQ ID No. 29) not extended except for a trace amount of the +1 product when dATP is used. Lanes 12–17 are controls; lane 10 is unused.

Example 9

Primer masking using blocking oligos

The ability of DNA polymerase to extend primers sequestered in blocking oligo-primer duplexes was examined. Primer sequence 18 (SEQ ID No. 32) was labeled at the 5' end using $\gamma$-$^{32}$P-ATP and polynucleotide kinase. Masked duplexes consisting of primer sequence 18 (SEQ ID No. 32) and either hairpin masking probe 18a* (SEQ ID No. 33) or 18b* (SEQ ID No. 34, see below) were incubated in 1x PCR buffer, (Perkin-Elmer Corp). supplemented with 2.5 mM $MgCl_{2, 200}$ mM each dNTP, and 1.25 units/reaction Taq polymerase ("Taq" in Figure) or Stoffel buffer, (Perkin-Elmer Corp). containing 2.5 mM $MgCl_{2, 200}$ mM each dNTP, and 2.5 units/reaction Stoffel polymerase ("St" in FIG. 11) in a volume of 50 μl.

| Probe No. | | SEQ ID No. |
|---|---|---|
| 18 | 5' GAATTGGCTGTCAACATAGCAGAAT | 32 |
| 18a* | 3' pCTTAACCCACAGTT—TATCGTCTTACGGCCTTTTGGCCG | 33 |
| 18b* | 3' pCTTAACCCACAGTT—TATCGTCT<u>GT</u>CGGCCTTTTGGCCG | 34 |

Reaction mixtures were incubated at 50° C. for 5 minutes. Fifteen microliter samples were removed at time zero and after the 5 minute incubation and mixed with an equal volume of formamide loading buffer. Samples were analyzed by electrophoresis through a 20% acrylamide/8M urea gel.

Figure 11:
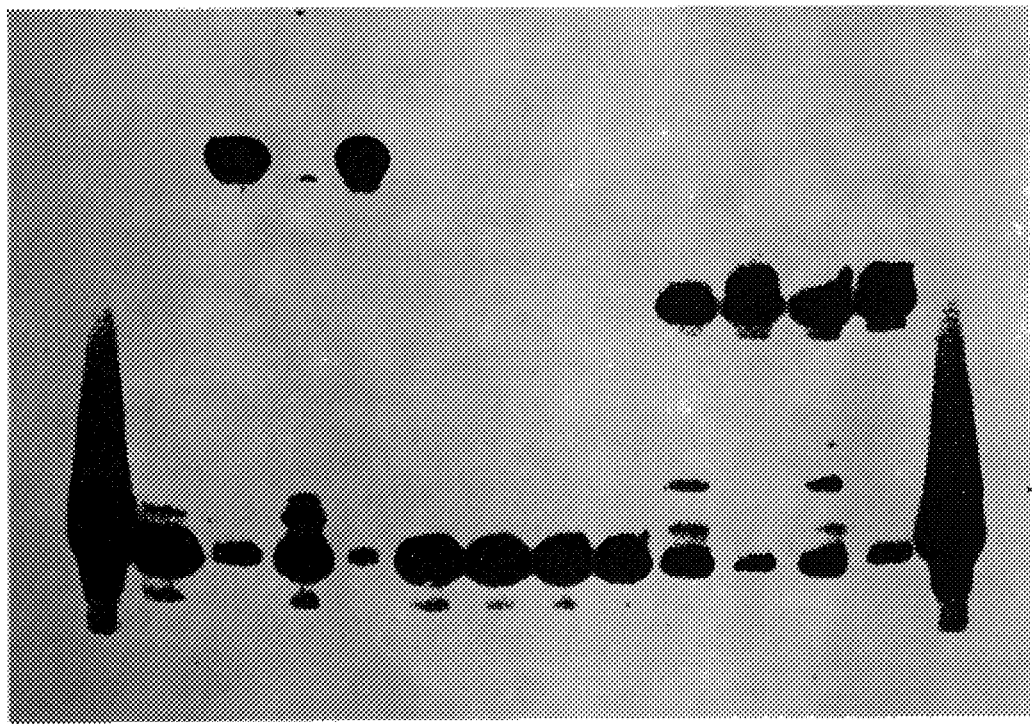
FIG. 11 is a print of an autoradiograph described in detail in Example 9. Lanes are numbered 1 to 14 across the bottom. Further information is found below the lane numbers as follows: M is a size marker lane; 0 and 5 refer to the time of incubation; "Taq" refers to reactions using PCR buffer with Taq polymerase; "St" refers to reactions using Stoffel buffer with the Stoffel fragment of polymerase; "hairpin", "hairpin+mismatch" and "controls" refer to the probe compositions in the series of reactions as is detailed in the example.

The results are shown in FIG. 11. The ability of either polymerase to extend the primer 18 (SEQ ID No. 32) using a blocking oligo as a template is shown in lanes 2–9. A hairpin structure alone (blocking oligo 18a* ; SEQ ID No. 33) provides only limited blocking of the polymerase extension (lanes 2–5). However, the use of blocking oligo 18b* (SEQ ID No. 34) having two mismatches with respect to the 3' end of primer 18 (see double underline under GT), as well as a hairpin structure, is sufficient to block extension of the primer (lanes 6–9). Lanes 10–13 are controls showing extension of the primer on a similar template containing an 8 base 5' overhang. It is believed that hairpin 18a* (SEQ ID No. 33) would provide improved abililty to block if the hairpin was covalently closed using a psoralen or similar crosslinking agent as described herein.

Examples 10–11

HIV PCR with blocking oligos

Target-specific primers were designed to amplify and detect the target sequence corresponding to the HIV-1 tat region. Shown below are primers 19 (SEQ ID No. 35) and 20 (SEQ ID No. 36), which have been reported by Chou et al, *Nucl. Acids Res.* 20:1717–1723 ( 1992) for amplification of HIV-1. The blocking oligos, indicated below by an asterisk, are discussed with the corresponding example.

Example 11

Two blocking oligos; locked hairpin/mismatched 5' ends

Example 10 is repeated except prior to performing the PCR reactions, the blocking oligos 19a* and 20a* (SEQ ID Nos 37 and 38) are separately reacted with a psoralen crosslinking agent under hybridizing conditions to covalently crosslink the hairpin end in a "closed" configuration. This secondary structure resists unfolding and, along with the mismatched bases, enhances the blocking ability.

Example 12

Two blocking oligos; blocking moiety modified 5' ends

Blocking oligos 19b* and 20b* (SEQ ID Nos. 39 and 40) were designed to be complementary to the PCR primers as shown. Each blocking oligo has a terminal 3' phosphate to prevent extension. The dashes represent nucleotides which were deleted in the blocking oligos to affect Tm as described herein. The underlined sequences (5'-extension) in blocking oligos 19b* (SEQ ID No. 39) and 20b* (SEQ ID No. 40) have the potential to form a hairpin loop structure, even when hybridized to their primer. The double underlined bases indicate mismatches with respect to the 3' end of the primer as before. dU replaces dT in these blocking oligos.

| Probe No. | | SEQ ID. No. |
|---|---|---|
| 19   | 5'   GAATTGGGTGTCAACATAGCAGAAT | 35 |
| 19a* | 3' pCTTAACCCACAGTT—TATCGTCTCCCGGCCTTTTGGCCG | 37 |
| 19b* | 3' pCUUAACCCACAGUU—UAUCGUCUCCCGGCCUUUUGGCCG | 39 |
| 20   | TCGTTATCAACACACCTGGTATCATAA 5' | 36 |
| 20a* | GGCCTTTTGGCCCCCAATAGTTGT—TGGACCATAGTATTp 3' | 38 |
| 20b* | GGCCUUUUGGCCCCCAAUAGUUGU—UGGACCAUAGUAUUp 3' | 40 |

Example 10

Two blocking oligos; hairpin/mismatched 5' ends

Blocking oligos 19a* and 20a* (SEQ ID Nos 37 and 38) were designed to be complementary to the PCR primers as shown. Each blocking oligo has a terminal 3' phosphate to prevent extension. The dashes represent nucleotides which were deleted in the blocking oligos to affect Tm as described herein. The underlined sequences (5'-extension) in blocking oligos 19a* (SEQ ID No. 37) and 20a* (SEQ ID No. 38) have the potential to form a hairpin loop structure, even when hybridized to their primer. The double underlined bases indicate mismatches with respect to the 3' end of the primer to enhance the blocking ability as shown in Example 9.

PCR is performed using standard conditions known in the art. Following amplification, reaction products could be detected via agarose gel electrophoresis and ethidium bromide staining, by hybridization with a specific internal probe, or by any other technique known in the art.

Just prior to performing PCR, the oligo:probe heteroduplexes are treated with uracil N-glycosylase (U.S. Pat. No. 5,035,996, Life Technologies, Inc.). This creates an abasic site which is heat labile. PCR is performed using standard conditions as before. Under the conditions of thermal cycling, the blocking oligos are cleaved at the abasic site. This reduces the Tm of the blocking oligo duplex, destabilizing it to reduce its interference in the amplification reaction.

While the above examples serve to illustrate the invention, the invention is not limited to the specific embodiments of the examples. Rather the invention is defined by the appended claims.

What is claimed is:

1. In a method for amplifying nucleic acids involving repeatedly extending one or more amplification probes by the template directed addition of individual nucleotides or oligonucleotide segments in the presence of blocking that are not extendible and that hybridize with amplification probes, the improvement comprising:

a) prior to initiating an amplification reaction, providing at least one amplification probe in a masked form, the mask consisting essentially of a blocking oligo hybridized with said amplification probe to form a blocking oligo-amplification-probe heteroduplex, wherein said blocking oligo-amplification probe heteroduplex has a $K_{50\ blocking\ oligo-probe}$ such that $K_{50\ blocking\ oligo\ probe}$ is less than $K_{50\ probe-target}$, wherein $K_{50\ probe-target}$ is the $K_{50}$ of a target strand-amplification probe homoduplex, and wherein said blocking oligo inhibits extension of the amplification probe prior to the amplfication reaction;

(b) denaturing the blocking oligo from the amplification probe to unmask the amplification probe; and c) carrying out the amplification reaction with the unmasked amplification probe;

wherein said blocking oligo is inhibited from interfering in the amplification reaction without physically removing the blocking oligo from the amplification mixture such that blocking oligo-amplification probe heteroduplexes and blocking oligo-target heteroduplexes do not form in substantial amounts during the amplification reaction.

2. The method of claim 1 wherein said inhibiting step is accomplished by using a blocking oligo that has at least one deletion or mismatch with respect to the amplification probe.

3. The method of claim 2 wherein the $K_{50}$ of said blocking oligo-amplification probe heteroduplex is 3° to 15° C. lower than the amplification probe-target homoduplex.

4. The method of claim 1 wherein the inhibiting step is accomplished by hybridizing the blocking oligo to a complementary blocking oligo to form a blocking oligo homoduplex which effectively sequesters both blocking oligos from the reaction.

5. The method of claim 4 wherein blocking oligo homoduplexes are preferentially favored over masked probe heteroduplexes by employing complementary tails on the blocking oligos which increase the $K_{50}$ the blocking oligo homoduplexes.

6. The method of claim 5 wherein said tails are from 5 to about 30 nucleotides long.

7. The method of claim 4 wherein the blocking oligo is covalently coupled to the complementary blocking oligo to permanently remove the blocking oligo homoduplex from the amplification reaction after denaturing the blocking oligo from the amplification probe and prior to carrying out the amplification reaction.

8. The method of claim 7 wherein said covalent coupling is accomplished by linking photoactivatable groups or chemical coupling groups present on the blocking oligos.

9. The method of claim 1 wherein the blocking oligo includes a 5' extension overhanging the 3' end of the amplification probe in the blocking oligo-amplification probe heteroduplex.

10. The method of claim 9 wherein said 5' overhanging extension is capable of forming a secondary structure.

11. The method of claim 10 wherein said 5' extension forms a hairpin turn on itself.

12. The method of claim 9 wherein the first nucleotide in the extension beyond the 3' end of the amplification probe is a stop base which inhibits extension by a polymerase past said stop base.

13. The method of claim 1 wherein the blocking oligo includes a 5' blocking moiety that prevents extension and tailing of the amplification probe in the blocking oligo-amplification probe heteroduplex.

14. The method of claim 1 wherein the blocking oligo includes means for effecting cleavage or degradation of the blocking oligo upon initiation of amplification.

15. The method of claim 14 wherein said effecting cleavage or degradation includes treatment with deoxyuracil N-glycosylase followed by thermal cycling.

16. The method of claim 1 wherein said amplification reaction is a polymerase chain reaction using at least two amplification probes which are primers, both of which are supplied prior to amplification in masked probe form.

17. The method of claim 1 wherein said amplification reaction is a ligase chain reaction using at least four amplification probes, at least two of which are supplied prior to amplification in masked probe form.

18. The method of claim 17 wherein said ligase chain reaction is a gap ligase chain reaction using two probes that must be extended to fill in the gaps, and the two amplification probes that are initially masked are the two that are extended.

19. The method of claim 17 wherein a common blocking oligo masks two amplification probes simultaneously.

20. The method of claim 17 wherein all four amplification probes are supplied prior to amplification in masked probe form.

* * * * *

UNITED STATES PATENT AND TRADEMARK OFFICE
CERTIFICATE OF CORRECTION

PATENT NO. : 5,814,492
DATED : September 29, 1998
INVENTOR(S) : Carrino et al.

It is certified that error appears in the above-identified patent and that said Letters Patent is hereby corrected as shown below:

Column 43, line 51, change "blocking" to --blocking probes--.

Column 43, line 52, change "with" to --with the--.

Signed and Sealed this

Second Day of March, 1999

Attest:

Q. TODD DICKINSON

*Attesting Officer*                *Acting Commissioner of Patents and Trademarks*

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:1:

GCTTTGAGTT CTGCTTCCTC CTTG         24

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:2:

GGAGGAAGCA GAACTCAAAG C         21

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:3:

GCTCTGCCTG TGGGGAATCC T         21

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:4:

AGGATTCCCC ACAGGCAGAG CTTG         24

( 2 ) INFORMATION FOR SEQ ID NO:5:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Chlamydia trachomatis ( x i ) SEQUENCE DESCRIPTION: SEQ ID NO:5:

GCTTTGAGTT CTGCTTCCTC CTTGCAAGCT CTGCCTGTGG GGAATCCT    48

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:6:

GGCCTTTTTG GCCCAAGGAG GAAGCAAACT CAAAGC    36

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:7:

GCTTTGAGTT TGCTTCCTCC    20

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:8:

AGGATTCCCC CAGGCAGAGC    20

( 2 ) INFORMATION FOR SEQ ID NO:9:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:9:

GGCCTTTTTG GCCCAAGCTC TGCCTGGGGG AA    32

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:10:

CCCCAAGGAG GAAGCAAACT CAAAGC    26

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:11:

CCCCAAGCTC TGCCTGGGGG AA        22

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:12:

CCCCAAGGAG GAAGCAAACT CAAAGC        26

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:13:

GCTTTGAGTT TGCTTCCTCC        20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:14:

AGGATTCCCC CAGGCAGAGC        20

( 2 ) INFORMATION FOR SEQ ID NO:15:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:15:

CCCCAAGCTC TGCCTGGGGG AATCCT        26

( 2 ) INFORMATION FOR SEQ ID NO:16:

( i ) SEQUENCE CHARACTERISTICS:
        ( A ) LENGTH: 23 base pairs ( B ) TYPE: nucleic acid
( C ) STRANDEDNESS: single
( D ) TOPOLOGY: linear ( i i ) MOLECULE TYPE: other (synthetic DNA)

( x i ) SEQUENCE DESCRIPTION: SEQ ID NO:16:

TTAGGAGGAA GCAAACTCAA AGC 23

( 2 ) INFORMATION FOR SEQ ID NO:17:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: other (synthetic DNA)

( x i ) SEQUENCE DESCRIPTION: SEQ ID NO:17:

TTAGCTCTGC CTGGGGGAA 19

( 2 ) INFORMATION FOR SEQ ID NO:18:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other (synthetic DNA)

( x i ) SEQUENCE DESCRIPTION: SEQ ID NO:18:

CCTCACAATA CCGCAGAGTC TAGA 24

( 2 ) INFORMATION FOR SEQ ID NO:19:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other (synthetic DNA)

( x i ) SEQUENCE DESCRIPTION: SEQ ID NO:19:

AGACTCTGCG GTATTGTGAG GATT 24

( 2 ) INFORMATION FOR SEQ ID NO:20:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other (synthetic DNA)

( x i ) SEQUENCE DESCRIPTION: SEQ ID NO:20:

GTGGTGGACT TCTCTCAATT TTCT 24

( 2 ) INFORMATION FOR SEQ ID NO:21:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: other (synthetic DNA)

( x i ) SEQUENCE DESCRIPTION: SEQ ID NO:21:

GAAAATTGAG AGAAGTCCAC CACGAG 26

( 2 ) INFORMATION FOR SEQ ID NO:22:

( i ) SEQUENCE CHARACTERISTICS:
        ( A ) LENGTH: 49 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Hepatitus B virus ( x i ) SEQUENCE DESCRIPTION: SEQ ID NO:22:

CCTCACAATA CCACAGAGTC TAGACTCGTG GTGGACTTCT CTCAATTTT 49

( 2 ) INFORMATION FOR SEQ ID NO:23:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:23:

CCTCACAATA CGCAGAGTCT AGA 23

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:24:

GAAAATTGAG AGAGTCCACC ACGAG 25

( 2 ) INFORMATION FOR SEQ ID NO:25:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:25:

GGCCTTTTGG CCTCTAGACT CTGCGTATTG TGAGG 35

( 2 ) INFORMATION FOR SEQ ID NO:26:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:26:

AGGCCTTTTG GCCTCTCGTG GTGGACTCTC TCAAT 35

( 2 ) INFORMATION FOR SEQ ID NO:27:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:27:

TCCACCACTC TTCTAGACT 19

( 2 ) INFORMATION FOR SEQ ID NO:28:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:28:

AGTCTCTCCT CGTGGTGGA 19

( 2 ) INFORMATION FOR SEQ ID NO:29:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:29:

AAGTTGTAAG CACGGATGAA TATGT 25

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:30:

ACATATTCAT CCGTGCTTAC AACT 24

( 2 ) INFORMATION FOR SEQ ID NO:31:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other (synthetic DNA)

( x i ) SEQUENCE DESCRIPTION: SEQ ID NO:31:

CATATTCATC CGTGCTTACA ACT 23

( 2 ) INFORMATION FOR SEQ ID NO:32:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: other (synthetic DNA)

( x i ) SEQUENCE DESCRIPTION: SEQ ID NO:32:

GAATTGGGTG TCAACATAGC AGAAT                                25

( 2 ) INFORMATION FOR SEQ ID NO:33:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: other (synthetic DNA)

( x i ) SEQUENCE DESCRIPTION: SEQ ID NO:33:

GCCGGTTTTC CGGCATTCTG CTATTTGACA CCCAATTC                  38

( 2 ) INFORMATION FOR SEQ ID NO:34:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( i i ) MOLECULE TYPE: other (synthetic DNA)

( x i ) SEQUENCE DESCRIPTION: SEQ ID NO:34:

GCCGGTTTTC CGGCTGTCTG CTATTTGACA CCCAATTC                  38

( 2 ) INFORMATION FOR SEQ ID NO:35:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: other (synthetic DNA)

( x i ) SEQUENCE DESCRIPTION: SEQ ID NO:35:

GAATTGGGTG TCAACATAGC AGAAT                                25

( 2 ) INFORMATION FOR SEQ ID NO:36:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: other (synthetic DNA)

( x i ) SEQUENCE DESCRIPTION: SEQ ID NO:36:

AATACTATGG TCCACACAAC TATTGCT                              27

( 2 ) INFORMATION FOR SEQ ID NO:37:

( i ) SEQUENCE CHARACTERISTICS:
    ( A ) LENGTH: 38 base pairs
    ( B ) TYPE: nucleic acid
    ( C ) STRANDEDNESS: single -continued

```
         ( D ) TOPOLOGY: linear ( i i ) MOLECULE TYPE: other (synthetic DNA)

( x i ) SEQUENCE DESCRIPTION: SEQ ID NO:37:

GCCGGTTTTC  CGGCCCTCTG  CTATTGACA  CCCAATTC                                      3 8

( 2 ) INFORMATION FOR SEQ ID NO:38:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( i i ) MOLECULE TYPE: other (synthetic DNA)

( x i ) SEQUENCE DESCRIPTION: SEQ ID NO:38:

GGCCTTTTGG  CCCCCAATAG  TTGTTGGACC  ATAGTATT                                     3 8

( 2 ) INFORMATION FOR SEQ ID NO:39:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( i i ) MOLECULE TYPE: other (synthetic DNA)

( x i ) SEQUENCE DESCRIPTION: SEQ ID NO:39:

GCCGGUUUUC  CGGCCCUCUG  CUAUUUGACA  CCCAAUUC                                     3 8

( 2 ) INFORMATION FOR SEQ ID NO:40:

( i ) SEQUENCE CHARACTERISTICS:
         ( A ) LENGTH: 38 base pairs
         ( B ) TYPE: nucleic acid
         ( C ) STRANDEDNESS: single
         ( D ) TOPOLOGY: linear ( i i ) MOLECULE TYPE: other (synthetic DNA)

( x i ) SEQUENCE DESCRIPTION: SEQ ID NO:40:

GGCCUUUUGG  CCCCCAAUAG  UUGUUGGACC  AUAGUAUU                                     3 8
```